(12) United States Patent
Crowe et al.

(10) Patent No.: US 10,772,839 B2
(45) Date of Patent: Sep. 15, 2020

(54) COMPOSITIONS

(71) Applicant: VHSQUARED LIMITED, Cambridge (GB)

(72) Inventors: Scott Crowe, Cambridge (GB); Mike West, Cambridge (GB); Kevin Roberts, Cambridge (GB); Tim Carlton, Cambridge (GB); Luana Maggiore, Cambridge (GB); Marion Cubitt, Cambridge (GB); Gary Whale, Cambridge (GB); John Wahlich, Cambridge (GB); Mike Frodsham, Deeside (GB)

(73) Assignee: VHsquared Limited, Babraham, Cambridge (GB)

( * ) Notice: Subject to any disclaimer, the term of this patent is extended or adjusted under 35 U.S.C. 154(b) by 0 days.

(21) Appl. No.: 16/140,843

(22) Filed: Sep. 25, 2018

(65) Prior Publication Data

US 2019/0008778 A1     Jan. 10, 2019

Related U.S. Application Data

(63) Continuation of application No. PCT/EP2017/057775, filed on Mar. 31, 2017.

(30) Foreign Application Priority Data

Mar. 31, 2016 (EP) .................................... 16163178

(51) Int. Cl.
*A61K 9/20* (2006.01)
*A61K 9/14* (2006.01)
(Continued)

(52) U.S. Cl.
CPC .............. *A61K 9/2095* (2013.01); *A61K 9/14* (2013.01); *A61K 9/16* (2013.01); *A61K 9/20* (2013.01);
(Continued)

(58) Field of Classification Search
CPC .. A61K 9/2095; A61K 9/2846; A61K 9/2853; A61K 9/50; A61K 9/4891;
(Continued)

(56) References Cited

U.S. PATENT DOCUMENTS 5,780,028 A * 7/1998 Graham ............... A61K 9/2004
424/130.1
2006/0057197 A1   3/2006 Han et al.
(Continued)

FOREIGN PATENT DOCUMENTS

WO    WO-9300077 A1    1/1993
WO    WO-2004041867 A2    5/2004
(Continued)

OTHER PUBLICATIONS

2005 Drug Bank Data (https://www.drugbank.ca/drugs/DB00085) for Pancrelipase.*

(Continued)

*Primary Examiner* — Blessing M Fubara
(74) *Attorney, Agent, or Firm* — Nutter McClennen & Fish LLP

(57) ABSTRACT

There is provided a solid pharmaceutical composition for delivering by oral administration a pharmaceutically active binding polypeptide to a region of the intestinal tract comprising a compressed core, wherein the compressed core comprises a pharmaceutically active binding polypeptide and wherein the compressed core is coated with a pH sensitive enteric coating.

21 Claims, 12 Drawing Sheets

Specification includes a Sequence Listing.

(51) Int. Cl.
  *A61K 9/50* (2006.01)
  *A61K 9/16* (2006.01)
  *A61K 9/28* (2006.01)
  *A61K 9/48* (2006.01)
  *A61K 9/00* (2006.01)

(52) U.S. Cl.
  CPC .......... *A61K 9/2846* (2013.01); *A61K 9/2853* (2013.01); *A61K 9/2866* (2013.01); *A61K 9/4891* (2013.01); *A61K 9/50* (2013.01); *A61K 9/0002* (2013.01)

(58) Field of Classification Search
  CPC ... A61K 9/14; A61K 9/16; A61K 9/20; A61K 9/2866; A61K 9/0002
  See application file for complete search history.

(56) References Cited

U.S. PATENT DOCUMENTS

| | | | |
|---|---|---|---|
| 2010/0260857 A1* | 10/2010 | Fallon | A61K 9/5063 424/491 |
| 2014/0170212 A1* | 6/2014 | Ortenzi | A61K 9/1617 424/451 |
| 2017/0002069 A1 | 1/2017 | Crowe et al. | |
| 2018/0009881 A1 | 1/2018 | Crowe et al. | |

FOREIGN PATENT DOCUMENTS

| | | |
|---|---|---|
| WO | WO-2006138181 A2 | 12/2006 |
| WO | WO-2008031770 A2 | 3/2008 |
| WO | WO-2008039761 A2 | 4/2008 |
| WO | WO-2008122965 A2 | 10/2008 |
| WO | WO-2008149143 A2 | 12/2008 |
| WO | WO-2009064457 A2 | 5/2009 |
| WO | WO-2009064460 A2 | 5/2009 |
| WO | WO-2010077422 A2 | 7/2010 |
| WO | WO-2011098518 A2 | 8/2011 |
| WO | WO-2011009365 A2 | 9/2011 |
| WO | WO-2011112229 A2 | 9/2011 |
| WO | WO-2012130872 A1 | 10/2012 |
| WO | WO-2012151199 A1 | 11/2012 |
| WO | WO-2013173687 A1 | 11/2013 |
| WO | WO-2014030049 A2 | 2/2014 |
| WO | WO-2014141152 A2 | 9/2014 |
| WO | WO-2015058173 A1 | 4/2015 |
| WO | WO-2015176031 A2 | 11/2015 |

OTHER PUBLICATIONS

Binz H.K., et al., "Designing Repeat Proteins: Well-expressed, Soluble and Stable Proteins from Combinatorial Libraries of Consensus Ankyrin Repeat Proteins," *J. Mol. Biol.*, vol. 332, pp. 489-503 (2003).
Fadda H.M., et al., "Physiological bicarbonate buffers: stabilisation and use as dissolution media for modified release systems," *Int. J. Pharm.*, vol. 382, pp. 56-60 (2009).
Garbacz G., et al., "A dynamic system for the simulation of fasting luminal pH-gradients using hydrogen carbonate buffers for dissolution testing of ionsable compounds," *Eur. J. Pharm. Sci.*, vol. 51, pp. 224-231 (2014).
Goyanes A., et al., "Gastrointestinal release behaviour of modified-release drug products: Dynamic dissolution testing of mesalazine formulations," *Int. J. Pharm.*, vol. 484, pp. 103-108 (2015).
Griffiths K., et al., "Shark Variable New Antigen Receptor ($V_{NAR}$) Single Domain Antibody Fragments: Stability and Diagnostic Applications," *Antibodies*, vol. 2, pp. 66-81 (2013).
Guerra I., et al., "Management of inflammatory bowel disease in poor responders to infliximab," *Clinical and Exp. Gastro.*, vol. 7, pp. 359-367 (2014).
Hamers-Casterman C., et al., "Naturally occurring antibodies devoid of light chains," *Nature*, vol. 363, pp. 446-448 (Jun. 1993).

Harmsen M.M., et al., "Selection and optimization of proteolytically stable llama single-domain antibody fragments for oral immunotherapy," *Appl. Microbiol., Biotechnol.*, vol. 72, pp. 544-551 (2006).
Hendrickson B.A., et al., "Clinical Aspects and Pathophysiology of Inflammatory Bowel Disease," *Clin. Microbiol. Rev.*, vol. 15, No. 1, pp. 79-94 (Jan. 2002).
Hussack G., et al., "Engineered Single-Domain Antibodies with High Protease Resistance and Thermal Stability," *PLOS One*, vol. 6, No. 11, pp. e28218-1-e281218-15 (Nov. 2011).
Hussan S.D., et al., "A review on recent advances on enteric coating," *IOSR J. Pharm.*, vol. 2, No. 6, 8 pages (Nov.-Dec. 2012).
McCoy L.E., et al., Neutralisation of HIV-1 cell-cell spread by human and llama antibodies, *Retrovirology*, vol. 11, 15 pages (2014).
Merchant H.A., et al., "Predicting the gastrointestinal behavior of modified-release products: Utility of a novel dynamic dissolution test apparatus involving the use of bicarbonate buffers," *Int. J. Pharm.*, vol. 475, pp. 585-591 (2014).
Michael J.G., et al., "The Role of Digestive Enzymes in Orally Induced Immune Tolerance," *J. Mol. Cell. Immun.*, vol. 18, Nos. 9-10, pp. 1049-1054 (1989).
Muyldermans S., et al., "Sequence and structure of VH domain from naturally occurring camel heavy chain immunoglobulins lacking light chains," *Prot. Eng.*, vol. 7, No. 9, pp. 1129-1135 (1994).
Muyldermans S., "Nanobodies: Natural Single-Domain Antibodies," Annu. Rev. Biochem., vol. 82, pp. 775-797 (2013).
Ordas I., et al., "Anti-TNF Monoclonal Antibodies in Inflammatory Bowel Disease: Pharmacokinetics-Based Dosing Paradigms," *Clin. Pharm. Ther.*, vol. 91, No. 4, pp. 635-646 (Apr. 2012).
Padlan E.A., "Anatomy of the Antibody Molecule," *Mol. Immun.*, vol. 31, No. 3, pp. 169-217 (1994).
Roux K.H., et al., "Structural analysis of the nurse shark (new) antigen receptor (NAR): Molecular convergence of NAR nad unusual mammalian immunoglobulins," *Proc. Natl. Acad. Sci. USA*, vol. 95, pp. 11804-11809 (Sep. 1998).
Ungar B., et al., "Optimizing Anti-TNF-α Therapy: Serum Levels of Infliximab and Adalimumab Are Associated With Mucosal Healing in Patients With Inflammatory Bowel Diseases," *Clin. Gast. Hep.*, vol. 14, pp. 550-557 (2016).
Van Schie K.A., et al., "The antibody response against human and chimeric anti-TNF therapeutic antibodies primarily targets the TNF binding region," *Ann. Rheum. Dis.*, vol. 74, pp. 311-314 (2015).
Ward E.S., et al., "Binding activities of a repertoire of single immunoglobulin variable domains secreted from *Escherichia coli,*" *Nature*, vol. 341, pp. 544-546 (Oct. 1989).
Crowe, S. et al, "Gastrointestinal Stability and Tissue Penetration of V565: a Novel Orally Administered Anti-TNF-alpha VorabodyTM," VHsquared, 10th Annual Proteins and Antibodies Congress (2017) (Poster).
Crowe, S. et al, "Gastrointestinal Stability and Tissue Penetration of V565: a Novel Orally Administered Anti-TNF-alpha VorabodyTM," PEGS Europe Protein and Antibody Engineering Summit (Nov. 13-17, 2017) (Poster I).
Crowe, S. et al, "Oral delivery of a novel engineered anti-TNF-alpha domain antibody (VorabodyTM) for the treatment of Intestinal Bowel Disease," VHsquared, PEGS Europe Protein and Antibody Engineering Summit (Nov. 13-17, 2017) (Poster II).
Crowe, S. et al, "Preclinical assessment of a novel anti-TNF-alpha VorabodyTM as an oral therapy for Crohn's Disease," VHsquared, 18th International Congress of Mucosal Immunology (Jul. 19-22, 2017) (Poster).
Crowe, S. et al, "Preclinical Development of a Novel, Orally-Administered Anti-Tumour Necrosis Factor Domain Antibody for the Treatment of Inflammatory Bowel Disease," Nature, Scientific Reports, vol. 8, 13 Pages (2018).
Nurbhai, S. et al, "Measured and Modelled Data Suggest that Oral Administration of V565, A Novel Domain Antibody to TNF-alpha, Could be Beneficial in the Treatment of IBD," VHsquared, 13th Congress of ECCO—Inflammatory Bowel Diseases (Feb. 14-17, 2018) (Poster).
Robinson, J. et al, "A Protease-resistant Oral Domain Antibody to TNF-alpha Delivers High Concentrations of Active Compound in

(56) References Cited

OTHER PUBLICATIONS

Ileal Fluid of Subjects with an Ileostomy," VHsquared, 25th United European Gastroenterology Week (Oct. 28-Nov. 1, 2017) (Poster).
Wahlich, J. et al, "Oral delivery of a novel domain antibody (VorabodyTM) for the treatment of Crohn's Disease," VHsquared, Global Conference on Pharmaceutics and Drug Delivery Systems (2017) (Poster).
West, M. et al, "Predicting intestinal tract luminal concentrations after oral dosing of an anti TNF-alpha domain antibody engineered for intestinal protease resistance," VHsquared, Antibody Engineering & Therapeutics (2017) (Poster).

* cited by examiner

SEQUENCE LISTING

```
<160> NUMBER OF SEQ ID NOS: 28

<210> SEQ ID NO 1
<211> LENGTH: 115
<212> TYPE: PRT
<213> ORGANISM: Artificial Sequence
<220> FEATURE:
<223> OTHER INFORMATION: Q62E10

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Thr Thr Ser Gly Leu Asp Phe Gly Ile His
            20                  25                  30

Trp Met Tyr Trp Phe Arg Gln Ala Pro Gly Lys Glu Leu Glu Trp Val
        35                  40                  45

Ala Glu Ile Asn Thr Asn Ala Leu Ile Thr Lys Tyr Ala Asp Ser Val
    50                  55                  60

Lys Gly Arg Phe Thr Ile Ser Arg Asp Asn Ala Lys Asn Thr Leu Phe
```

```
                65                  70                  75                  80
Leu Gln Met Asn Asp Leu Lys Ser Glu Asp Thr Ala Val Tyr Tyr Cys
                    85                  90                  95

Ser Asn Thr Gln Asn Gly Ala Ala Lys Gly Gln Gly Val Gln Val Thr
                100                 105                 110

Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Q65F2

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Ser His
                20                  25                  30

Trp Met Tyr Trp Val Arg Gln Ala Pro Gly Lys Gly Leu Glu Trp Val
            35                  40                  45

Ser Glu Ile Asn Thr Asn Gly Leu Ile Thr Ser Tyr Val Asp Ser Val
        50                  55                  60

Lys Gly Arg Phe Thr Val Ser Arg Asp Asn Ala Asn Thr Leu Tyr
65                  70                  75                  80

Leu Glu Met Thr Ser Leu Glu Pro Glu Asp Thr Ala Leu Tyr Tyr Cys
                    85                  90                  95

Ala Arg Asn Gln Lys Gly Leu Asn Lys Gly Gln Gly Thr Gln Val Thr
                100                 105                 110

Val Ser Ser
        115

<210> SEQ ID NO 3
<211> LENGTH: 115
<212> TYPE: PRT
<213> ORGANISM: Artificial Sequence
<220> FEATURE:
<223> OTHER INFORMATION: Q65F3

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Ser His
                20                  25                  30

Trp Met Tyr Trp Val Arg Gln Ala Pro Gly Lys Gly Leu Glu Trp Val
            35                  40                  45

Ser Glu Ile Asn Thr Asn Gly Leu Ile Thr Lys Tyr Ile Asp Ser Val
        50                  55                  60

Arg Gly Arg Phe Thr Ala Ser Arg Asp Asn Ala Asn Thr Leu Tyr
65                  70                  75                  80

Leu Glu Met Thr Asn Leu Glu Pro Glu Asp Thr Ala Leu Tyr Tyr Cys
                    85                  90                  95

Ala Arg Asn Gln Lys Gly Leu Asn Lys Gly Gln Gly Thr Gln Val Thr
                100                 105                 110

Val Ser Ser
        115
```

<210> SEQ ID NO 4
<211> LENGTH: 115
<212> TYPE: PRT
<213> ORGANISM: Artificial Sequence
<220> FEATURE:
<223> OTHER INFORMATION: Q62F2

<400> SEQUENCE: 4

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Asn Ser His
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Asn Tyr Val Asp Ser Val
    50                  55                  60

Lys Gly Arg Phe Thr Val Ser Arg Asp Asn Ala Ala Asn Thr Leu Tyr
65                  70                  75                  80

Leu Glu Met Thr Ser Leu Lys Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: Q65G1

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Asp Phe Tyr Ser His
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Ile Asp Ser Val
    50                  55                  60

Arg Gly Arg Phe Thr Val Ser Arg Asp Asn Ala Ala Asn Thr Leu Tyr
65                  70                  75                  80

Leu Glu Met Thr Asn Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115

<210> SEQ ID NO 6
<211> LENGTH: 115
<212> TYPE: PRT
<213> ORGANISM: Artificial Sequence
<220> FEATURE:
<223> OTHER INFORMATION: Q65H6

<400> SEQUENCE: 6

Glu Val Gln Leu Val Glu Ser Gly Gly Gly Leu Val Gln Pro Gly Gly

```
                1               5                      10                      15
          Ser Leu Arg Leu Ser Cys Val Ala Ser Gly Phe Asp Phe Tyr Ser His
                         20                      25                      30

Trp Met Tyr Trp Val Arg Gln Ala Pro Gly Lys Gly Leu Glu Trp Val
                         35                      40                      45

Ser Glu Ile Asn Thr Asn Gly Leu Ile Thr Lys Tyr Ile Asp Ser Val
                         50                      55                      60

Arg Gly Arg Phe Thr Val Ser Arg Asp Asn Ala Ala Asn Thr Leu Tyr
          65                      70                      75                      80

Leu Glu Met Thr Asn Leu Glu Pro Glu Asp Thr Ala Leu Tyr Tyr Cys
                         85                      90                      95

Ala Arg Asn Gln Lys Gly Leu Asn Lys Gly Gln Gly Thr Gln Val Thr
                         100                     105                     110

Val Ser Ser
                 115
```

<210> SEQ ID NO 7
<211> LENGTH: 115
<212> TYPE: PRT
<213> ORGANISM: Artificial Sequence
<220> FEATURE:
<223> OTHER INFORMATION: Q65F1

<400> SEQUENCE: 7

```
          Glu Val Gln Leu Val Glu Ser Gly Gly Gly Leu Val Gln Pro Gly Gly
          1               5                      10                      15

Ser Leu Arg Leu Ser Cys Ala Ala Ser Gly Phe Asp Phe Gly Val His
                         20                      25                      30

Trp Met Tyr Trp Val Arg Gln Ala Pro Gly Lys Gly Leu Glu Trp Val
                         35                      40                      45

Ser Glu Ile Asn Thr Asn Gly Leu Ile Thr Lys Tyr Ile Asp Ser Val
                         50                      55                      60

Gly Gly Arg Phe Thr Val Ser Arg Asp Asn Ala Ala Asn Arg Leu Tyr
          65                      70                      75                      80

Leu Glu Met Thr Asn Leu Glu Pro Glu Asp Thr Ala Leu Tyr Tyr Cys
                         85                      90                      95

Ala Arg Asn Gln Met Gly Leu Asn Lys Gly Gln Gly Thr Gln Val Thr
                         100                     105                     110

Val Ser Ser
                 115
```

<210> SEQ ID NO 8
<211> LENGTH: 115
<212> TYPE: PRT
<213> ORGANISM: Artificial Sequence
<220> FEATURE:
<223> OTHER INFORMATION: Q65D1

<400> SEQUENCE: 8

```
          Glu Val Gln Leu Val Glu Ser Gly Gly Gly Leu Val Gln Pro Gly Gly
          1               5                      10                      15

Ser Leu Arg Leu Ser Cys Thr Ala Ser Gly Phe Asp Phe Asp Asn His
                         20                      25                      30

Trp Met Cys Trp Val Arg Gln Ala Pro Gly Lys Gly Leu Glu Trp Val
                         35                      40                      45

Ser Glu Ile Asn Thr Asn Gly Leu Ile Thr Lys Tyr Ala Asp Phe Val
                         50                      55                      60
```

```
Lys Gly Arg Phe Thr Val Ser Arg Asp Asn Ala Ala Asn Thr Leu Tyr
 65                  70                  75                  80

Leu Gln Ile Thr Arg Leu Lys Pro Glu Asp Thr Ala Leu Tyr Tyr Cys
                 85                  90                  95

Ala Arg Asn Gln Lys Gly Leu Asn Lys Gly Gln Gly Thr Gln Val Thr
            100                 105                 110

Val Ser Ser
        115

<210> SEQ ID NO 9
<211> LENGTH: 115
<212> TYPE: PRT
<213> ORGANISM: Artificial Sequence
<220> FEATURE:
<223> OTHER INFORMATION: Q65C7

<400> SEQUENCE: 9

Glu Val Gln Leu Val Glu Ser Gly Gly Gly Leu Val Gln Pro Gly Arg
  1               5                  10                  15

Ser Leu Arg Leu Ser Cys Thr Ala Ser Gly Phe Asp Phe Ser Ser His
             20                  25                  30

Trp Met Tyr Trp Val Arg Gln Ala Pro Gly Lys Gly Leu Glu Trp Val
         35                  40                  45

Ser Glu Ile Asn Thr Asn Gly Leu Ile Thr Lys Tyr Ala Asp Phe Val
 50                  55                  60

Lys Gly Arg Phe Thr Val Ser Arg Asp Asn Ala Ala Asn Thr Leu Tyr
 65                  70                  75                  80

Leu Glu Ile Thr Arg Leu Glu Pro Glu Asp Thr Ala Leu Tyr Tyr Cys
                 85                  90                  95

Ala Arg Asn Gln Lys Gly Leu Asn Lys Gly Gln Gly Thr Gln Val Thr
            100                 105                 110

Val Ser Ser
        115

<210> SEQ ID NO 10
<211> LENGTH: 115
<212> TYPE: PRT
<213> ORGANISM: Artificial Sequence
<220> FEATURE:
<223> OTHER INFORMATION: Q65D3

<400> SEQUENCE: 10

Glu Val Gln Leu Val Glu Ser Gly Gly Gly Leu Val Gln Pro Gly Gly
  1               5                  10                  15

Ser Leu Arg Leu Ser Cys Val Ala Ser Gly Phe Asp Phe Ser Ser His
             20                  25                  30

Trp Met Tyr Trp Val Arg Gln Ala Pro Gly Lys Gly Leu Glu Trp Val
         35                  40                  45

Ser Glu Ile Asn Thr Asn Gly Leu Ile Thr Lys Tyr Ala Asp Ser Thr
 50                  55                  60

Lys Gly Arg Phe Thr Val Ser Arg Asp Asn Ala Ala Asn Met Leu Asn
 65                  70                  75                  80

Leu Glu Met Thr Ser Leu Glu Pro Glu Asp Thr Ala Leu Tyr Tyr Cys
                 85                  90                  95

Ala Arg Asn Glu Arg Gly Leu Asn Lys Gly Gln Gly Thr Gln Val Thr
            100                 105                 110

Val Ser Ser
        115
```

```
<210> SEQ ID NO 11
<211> LENGTH: 115
<212> TYPE: PRT
<213> ORGANISM: Artificial Sequence
<220> FEATURE:
<223> OTHER INFORMATION: Q65B1

<400> SEQUENCE: 11
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Lys | Leu | Ser | Cys | Ala | Ala | Ser | Gly | Phe | Asp | Phe | Ser | Ser | His |
|---|---|---|---|---|---|---|---|---|---|---|---|---|---|---|---|
| | | | 20 | | | | | 25 | | | | | 30 | | |

| Trp | Met | Tyr | Trp | Val | Arg | Gln | Ala | Pro | Gly | Lys | Glu | Leu | Glu | Trp | Leu |
|---|---|---|---|---|---|---|---|---|---|---|---|---|---|---|---|
| | | 35 | | | | | 40 | | | | | 45 | | | |

| Ser | Glu | Ile | Asn | Thr | Asn | Gly | Leu | Ile | Thr | Lys | Tyr | Gly | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Val | Ser | Arg | Asn | Asn | Ala | Ala | Asn | Lys | Met | Tyr |
|---|---|---|---|---|---|---|---|---|---|---|---|---|---|---|---|
| 65 | | | | 70 | | | | | 75 | | | | | 80 | |

| Leu | Glu | Leu | Thr | Arg | Leu | Glu | Pro | Glu | Asp | Thr | Ala | Leu | Tyr | Tyr | Cys |
|---|---|---|---|---|---|---|---|---|---|---|---|---|---|---|---|
| | | | | 85 | | | | | 90 | | | | | 95 | |

| Ala | Arg | Asn | Gln | Lys | Gly | Leu | Asn | Lys | Gly | Gln | Gly | Thr | Gln | Val | Thr |
|---|---|---|---|---|---|---|---|---|---|---|---|---|---|---|---|
| | | | 100 | | | | | 105 | | | | | 110 | | |

| Val | Ser | Ser |
|---|---|---|
| | | 115 |

```
<210> SEQ ID NO 12
<211> LENGTH: 115
<212> TYPE: PRT
<213> ORGANISM: Artificial Sequence
<220> FEATURE:
<223> OTHER INFORMATION: Q65F6

<400> SEQUENCE: 12
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Phe | Asp | Phe | Gly | Ile | His |
|---|---|---|---|---|---|---|---|---|---|---|---|---|---|---|---|
| | | | 20 | | | | | 25 | | | | | 30 | | |

| Trp | Met | Tyr | Trp | Val | Arg | Gln | Ala | Pro | Gly | Lys | Glu | Leu | Glu | Trp | Val |
|---|---|---|---|---|---|---|---|---|---|---|---|---|---|---|---|
| | | 35 | | | | | 40 | | | | | 45 | | | |

| Ala | Glu | Ile | Asn | Thr | Asn | Gly | Leu | Ile | Thr | Leu | Tyr | Ser | Asp | Ser | Val |
|---|---|---|---|---|---|---|---|---|---|---|---|---|---|---|---|
| 50 | | | | | 55 | | | | | 60 | | | | | |

| Arg | Gly | Arg | Phe | Thr | Ala | Ser | Arg | Asp | Asn | Ala | Asn | Asn | Ala | Leu | Phe |
|---|---|---|---|---|---|---|---|---|---|---|---|---|---|---|---|
| 65 | | | | 70 | | | | | 75 | | | | | 80 | |

| Leu | Gln | Met | Asn | Asp | Leu | Lys | Phe | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Ser | Arg | Asn | Gly | Ala | Ala | Lys | Gly | Gln | Gly | Thr | Gln | Val | Thr |
|---|---|---|---|---|---|---|---|---|---|---|---|---|---|---|---|
| | | | 100 | | | | | 105 | | | | | 110 | | |

| Val | Ser | Ser |
|---|---|---|
| | | 115 |

```
<210> SEQ ID NO 13
<211> LENGTH: 115
<212> TYPE: PRT
<213> ORGANISM: Artificial Sequence
<220> FEATURE:
<223> OTHER INFORMATION: Q65F11

<400> SEQUENCE: 13
```

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Asp Phe Gly Ile His
            20                  25                  30

Trp Met Tyr Trp Val Arg Gln Ala Pro Gly Lys Glu Leu Glu Trp Val
        35                  40                  45

Ala Glu Ile Asn Thr Asn Gly Leu Ile Thr Leu Tyr Ser Asp Ser Val
    50                  55                  60

Arg Gly Arg Phe Thr Ala Ser Arg Asp Asn Ala Asn Asn Ala Leu Phe
65                  70                  75                  80

Leu Gln Met Asn Asp Leu Lys Phe Glu Asp Thr Ala Val Tyr Tyr Cys
                85                  90                  95

Ala Lys Ser Arg Asn Gly Ala Ala Lys Gly Gln Gly Thr Gln Val Thr
            100                 105                 110

Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: Q65E12

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Asp Phe Ser Ile His
            20                  25                  30

Trp Met Tyr Trp Val Arg Gln Ala Pro Gly Lys Glu Leu Glu Trp Val
        35                  40                  45

Ala Glu Ile Asn Thr Asn Gly Leu Ile Thr Leu Tyr Ala Asp Ser Val
    50                  55                  60

Lys Gly Arg Phe Thr Ala Ser Arg Asp Asn Ala Lys Asn Ala Leu Phe
65                  70                  75                  80

Leu Gln Met Asn Asp Leu Lys Phe Glu Asp Thr Ala Val Tyr Tyr Cys
                85                  90                  95

Ala Lys Ser Arg Asn Gly Ala Ala Gly Gly Gln Gly Thr Gln Val Thr
            100                 105                 110

Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: Q65C12

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Pro Phe Asp Ile His
            20                  25                  30

Trp Met Tyr Trp Val Arg Gln Ala Pro Gly Lys Glu Leu Glu Trp Val
        35                  40                  45

Ala Glu Ile Asn Thr Asn Ala Leu Ile Thr Thr Tyr Ala Asp Ser Val
    50                  55                  60

```
Lys Gly Arg Phe Thr Ile Ser Arg Asp Asn Ala Lys Asn Thr Leu Phe
 65                  70                  75                  80

Leu Gln Met Asn Asp Leu Lys Phe Glu Asp Thr Ala Val Tyr Tyr Cys
                 85                  90                  95

Thr His Ser Arg Asn Gly Ala Ala Lys Gly Gln Gly Thr Gln Val Thr
            100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: Q65A6

<400> SEQUENCE: 16

Glu Val Gln Leu Val Glu Ser Gly Gly Gly Leu Val Gln Pro Gly Gly
  1               5                  10                  15

Ser Leu Arg Leu Ser Cys Thr Ala Ser Gly Leu Asp Phe Gly Ile His
                 20                  25                  30

Trp Met Tyr Trp Val Arg Gln Ala Pro Gly Lys Glu Leu Glu Trp Val
             35                  40                  45

Ala Glu Ile Asn Thr Asn Gly Leu Ile Thr His Tyr Thr Asp Ser Val
         50                  55                  60

Ser Gly Arg Phe Thr Ile Ser Arg Asp Asn Ala Lys Asn Thr Leu Phe
 65                  70                  75                  80

Leu Gln Met Asn Asp Leu Lys Phe Glu Asp Thr Ala Val Tyr Ala Cys
                 85                  90                  95

Ala Thr Ser Arg Asn Gly Ala Ala Lys Gly Gln Gly Thr Gln Val Thr
            100                 105                 110

Val Ser Ser
        115

<210> SEQ ID NO 17
<211> LENGTH: 115
<212> TYPE: PRT
<213> ORGANISM: Artificial Sequence
<220> FEATURE:
<223> OTHER INFORMATION: Q65A3

<400> SEQUENCE: 17

Glu Val Gln Leu Val Glu Ser Gly Gly Gly Leu Val Gln Pro Gly Gly
  1               5                  10                  15

Ser Leu Arg Pro Ser Cys Thr Thr Ser Gly Leu Asp Phe Gly Ile His
                 20                  25                  30

Trp Met Tyr Trp Phe Arg Gln Ala Pro Gly Lys Glu Leu Glu Trp Val
             35                  40                  45

Ala Glu Ile Asn Thr Asn Ala Leu Ile Thr Lys Tyr Ala Asp Ser Val
         50                  55                  60

Lys Gly Arg Phe Thr Ile Ser Arg Asp Asn Ala Lys Asn Thr Leu Phe
 65                  70                  75                  80

Leu Gln Met Asn Asp Leu Lys Ser Glu Asp Thr Ala Val Tyr Tyr Cys
                 85                  90                  95

Ser Asn Thr Gln Asn Gly Ala Ala Lys Gly Gln Gly Val Gln Val Thr
            100                 105                 110

Val Ser Ser
```

<210> SEQ ID NO 18
<211> LENGTH: 115
<212> TYPE: PRT
<213> ORGANISM: Artificial Sequence
<220> FEATURE:
<223> OTHER INFORMATION: Q62F10

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Asp Phe Asn Ile His
            20                  25                  30

Trp Met Tyr Trp Val Arg Gln Ala Pro Gly Lys Glu Leu Glu Trp Val
        35                  40                  45

Ala Glu Ile Asn Thr Asn Gly Leu Ile Thr Val Tyr Pro Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Asn Leu Lys Phe Glu Asp Thr Ala Val Tyr Tyr Cys
                85                  90                  95

Thr Asn Thr Gln Asn Gly Lys Thr Lys Gly Gln Gly Thr Gln Val Thr
            100                 105                 110

Val Ser Ser
        115

<210> SEQ ID NO 19
<211> LENGTH: 115
<212> TYPE: PRT
<213> ORGANISM: Artificial Sequence
<220> FEATURE:
<223> OTHER INFORMATION: 1D7F-EV

<400> SEQUENCE: 19

Glu Val Gln Leu Val Glu Ser Gly Gly Gly Leu Val Gln Pro Gly Ala
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115

<210> SEQ ID NO 20
<211> LENGTH: 115
<212> TYPE: PRT
<213> ORGANISM: Artificial Sequence
<220> FEATURE:
<223> OTHER INFORMATION: 1D8F-EV

<400> SEQUENCE: 20

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
                100                 105                 110

Val Ser Ser
        115

<210> SEQ ID NO 21
<211> LENGTH: 115
<212> TYPE: PRT
<213> ORGANISM: Artificial Sequence
<220> FEATURE:
<223> OTHER INFORMATION: ID9F-EV

<400> SEQUENCE: 21

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
50                  55                  60

His Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
                100                 105                 110

Val Ser Ser
        115

<210> SEQ ID NO 22
<211> LENGTH: 115
<212> TYPE: PRT
<213> ORGANISM: Artificial Sequence
<220> FEATURE:
<223> OTHER INFORMATION: ID13F-EV

<400> SEQUENCE: 22

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val

```
            50                  55                  60
Lys Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                 85                  90                  95

Ala Arg Asn Gln His Gly Leu Asn Lys Gly Gln Gly Thr Gln Val Thr
                100                 105                 110

Val Ser Ser
        115

<210> SEQ ID NO 23
<211> LENGTH: 115
<212> TYPE: PRT
<213> ORGANISM: Artificial Sequence
<220> FEATURE:
<223> OTHER INFORMATION: ID14F-EV

<400> SEQUENCE: 23

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Asp Phe Ser Ser His
                 20                  25                  30

Trp Met Tyr Trp Val Arg Gln Ala Pro Gly Lys Glu Leu Glu Trp Leu
             35                  40                  45

Ser Glu Ile Asn Thr Asn Gly Leu Ile Thr Lys Tyr Gly Asp Ser Val
         50                  55                  60

Lys Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                 85                  90                  95

Ala Arg Asn Gln Lys Gly Leu Asn His Gly Gln Gly Thr Gln Val Thr
                100                 105                 110

Val Ser Ser
        115

<210> SEQ ID NO 24
<211> LENGTH: 115
<212> TYPE: PRT
<213> ORGANISM: Artificial Sequence
<220> FEATURE:
<223> OTHER INFORMATION: ID15F-EV

<400> SEQUENCE: 24

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Asp Phe Ser Ser His
                 20                  25                  30

Trp Met Tyr Trp Val Arg Gln Ala Pro Gly Lys Glu Leu Glu Trp Leu
             35                  40                  45

Ser Glu Ile Asn Thr Asn Gly Leu Ile Thr Lys Tyr Gly Asp Ser Val
         50                  55                  60

Lys Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                 85                  90                  95

Ala Arg Asn Gln His Gly Leu Asn His Gly Gln Gly Thr Gln Val Thr
                100                 105                 110
```

Val Ser Ser
        115

<210> SEQ ID NO 25
<211> LENGTH: 115
<212> TYPE: PRT
<213> ORGANISM: Artificial Sequence
<220> FEATURE:
<223> OTHER INFORMATION: Q62E10-DVQLV

<400> SEQUENCE: 25

Asp Val Gln Leu Val Glu Ser Gly Gly Gly Leu Val Gln Pro Gly Gly
1               5                   10                  15

Ser Leu Arg Leu Ser Cys Thr Thr Ser Gly Leu Asp Phe Gly Ile His
            20                  25                  30

Trp Met Tyr Trp Phe Arg Gln Ala Pro Gly Lys Glu Leu Glu Trp Val
        35                  40                  45

Ala Glu Ile Asn Thr Asn Ala Leu Ile Thr Lys Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Asp Leu Lys Ser Glu Asp Thr Ala Val Tyr Tyr Cys
                85                  90                  95

Ser Asn Thr Gln Asn Gly Ala Ala Lys Gly Gln Gly Val Gln Val Thr
            100                 105                 110

Val Ser Ser
        115

<210> SEQ ID NO 26
<211> LENGTH: 115
<212> TYPE: PRT
<213> ORGANISM: Artificial Sequence
<220> FEATURE:
<223> OTHER INFORMATION: ID34F

<400> SEQUENCE: 26

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser
        115

<210> SEQ ID NO 27
<211> LENGTH: 115
<212> TYPE: PRT
<213> ORGANISM: Artificial Sequence
<220> FEATURE:
<223> OTHER INFORMATION: ID37F -continued

```
<400> SEQUENCE: 27

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115

<210> SEQ ID NO 28
<211> LENGTH: 115
<212> TYPE: PRT
<213> ORGANISM: Artificial Sequence
<220> FEATURE:
<223> OTHER INFORMATION: ID38F

<400> SEQUENCE: 28

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser
        115
```

COMPOSITIONS

CROSS-REFERENCE TO RELATED APPLICATIONS

This application is a continuation-in-part of International Application No. PCT/EP2017/057775, filed on Mar. 31, 2017, which claims priority to European Application No. 16163178.3, filed on Mar. 31, 2016, the entire contents of which are hereby incorporated by reference.

FIELD OF THE INVENTION

The present invention relates to solid pharmaceutical compositions for the purpose of delivering by oral administration a pharmaceutically active binding polypeptide to a region of the intestinal tract. These compositions benefit from advantageous release profiles and may be used in the treatment of diseases of the intestinal tract. The present invention also relates to methods of delivering pharmaceutically active binding polypeptides to a region of the intestinal tract by oral administration.

BACKGROUND OF THE INVENTION

Diseases, such as inflammatory bowel disease, manifest in various regions of the intestinal tract, such as regions of the small intestine. There exist pharmaceutically active binding polypeptides which are effective in the treatment of inflammatory bowel disease when administered systemically. For example, anti-TNF-alpha antibodies have demonstrated efficacy in treating inflammatory bowel diseases. However, because these antibodies are commonly delivered by injection (i.e. intravenous, subcutaneous or intramuscular) and neutralise TNF-alpha systemically, their use may be associated with serious side effects, including reactivation of tuberculosis and a long-term risk of malignancy. Moreover, the parenteral route of administration and the large doses required make these antibody therapies expensive and hardly accessible for patients.

Oral administration of such polypeptides for local effect in a target region of the intestinal tract would be preferable, due to for example reduced cost and the convenience of this dosage form. In addition, oral administration may provide reduced immunogenicity as compared to parenteral administration forms and may reduce or eliminate unnecessary systemic exposure to the polypeptide.

To achieve this goal, a suitable release profile must be achieved. That is, the activity of the polypeptide must be maintained after transit through the upper intestinal tract including the stomach and suitably the duodenum and the desired dosage of active polypeptide must be delivered to the desired location of the intestinal tract.

Pharmaceutical compositions of the present invention may, in at least some embodiments, have one or more of the following advantages compared to those of the prior art:
(i) a sustained release profile,
(ii) a delayed release profile,
(iii) targeted release to one or more regions of the intestinal tract,
(iv) substantially consistent release to all regions of the intestinal tract from the duodenum to the anal canal (i.e. avoiding 'dose dumping'),
(v) reduced host immune response to the delivered polypeptide compared to parenteral administration,
(vi) reduced systemic exposure to pharmaceutically active agent,
(vii) reduced dosage required for therapeutic effects,
(viii) reduced cost of production,
(ix) maintained or improved thermal stability of polypeptide.

PRIOR ART

WO2014/030049 (D1) discloses compositions comprising a single variable domain and camostat mesylate as a means of stabilising a single variable domain, in particular in protease-rich environments such as the stomach and intestine. D1 exemplifies liquid compositions, which are injected directly into the gastrointestinal tract of mice.

US2010/260857 (D2) discloses coated digestive enzyme preparations. D2 exemplifies free-flowing digestive enzyme particles coated with lipids and packaged in a sachet or capsule.

WO2008/122965 (D3) discloses cyclosporin compositions in a solubilised liquid form.

US2006/057197 (D4) discloses pharmaceutical dosage forms for non-polypeptide, small molecules. All exemplification in D4 relates to the delivery of baclofen and subsequent monitoring of plasma profiles.

Hussan et al 2012 *IOSR Journal of Pharmacy* 2(6):5-11 (D5) is a review of recent advances in enteric coating.

Harmsen et al 2006 *Applied Microbiology and Biotechnology* 72(3):544-551 (D6) discloses the selection and optimization of proteolytically stable llama single-domain antibody fragments for oral immunotherapy. D6 provides no information on solid dosage forms.

Hussack et al 2011 *PLOS ONE* 6(11):e28218 (D7) discloses engineered single-domain antibodies with high protease resistance and thermal stability. D7 provides no information on solid dosage forms.

None of the above discloses a solid composition comprising a compressed core capable of sustained intestinal delivery of pharmaceutically active binding polypeptide.

SUMMARY OF THE INVENTION

The present inventors have produced surprisingly advantageous solid pharmaceutical formulations suitable for delivering by oral administration a pharmaceutically active binding polypeptide to a region of the intestinal tract. These pharmaceutical formulations are particularly advantageous due to their delayed and/or sustained release profiles. It may be expected that these pharmaceutical formulations have particular utility in the prevention or treatment of diseases of the intestinal tract such as autoimmune and/or inflammatory disease such as inflammatory bowel disease, or in the prevention or treatment of infection from an intestinal tract resident pathogenic microbe.

The present invention provides a solid pharmaceutical composition for delivering by oral administration a pharmaceutically active binding polypeptide to a region of the intestinal tract comprising a compressed core, wherein the compressed core comprises a pharmaceutically active binding polypeptide and wherein the compressed core is coated with a pH sensitive enteric coating.

Also provided is a solid pharmaceutical composition for use in the treatment of a disease of the intestinal tract by oral administration to a region of the intestinal tract comprising a compressed core, wherein the compressed core comprises a pharmaceutically active binding polypeptide and wherein the compressed core is coated with a pH sensitive enteric coating.

Also provided is a method of delivering a pharmaceutically active binding polypeptide to a region of the intestinal tract comprising orally administering a solid pharmaceutical composition comprising a compressed core, wherein the compressed core comprises a pharmaceutically active binding polypeptide and wherein the compressed core is coated with a pH sensitive enteric coating.

Also provided is a compressed core for a solid pharmaceutical composition wherein the composition is for delivering a pharmaceutically active binding polypeptide to a region of the intestinal tract by oral administration and wherein the compressed core comprises a pharmaceutically active binding polypeptide for local therapeutic effect.

DESCRIPTION OF THE SEQUENCES

Figure 1:
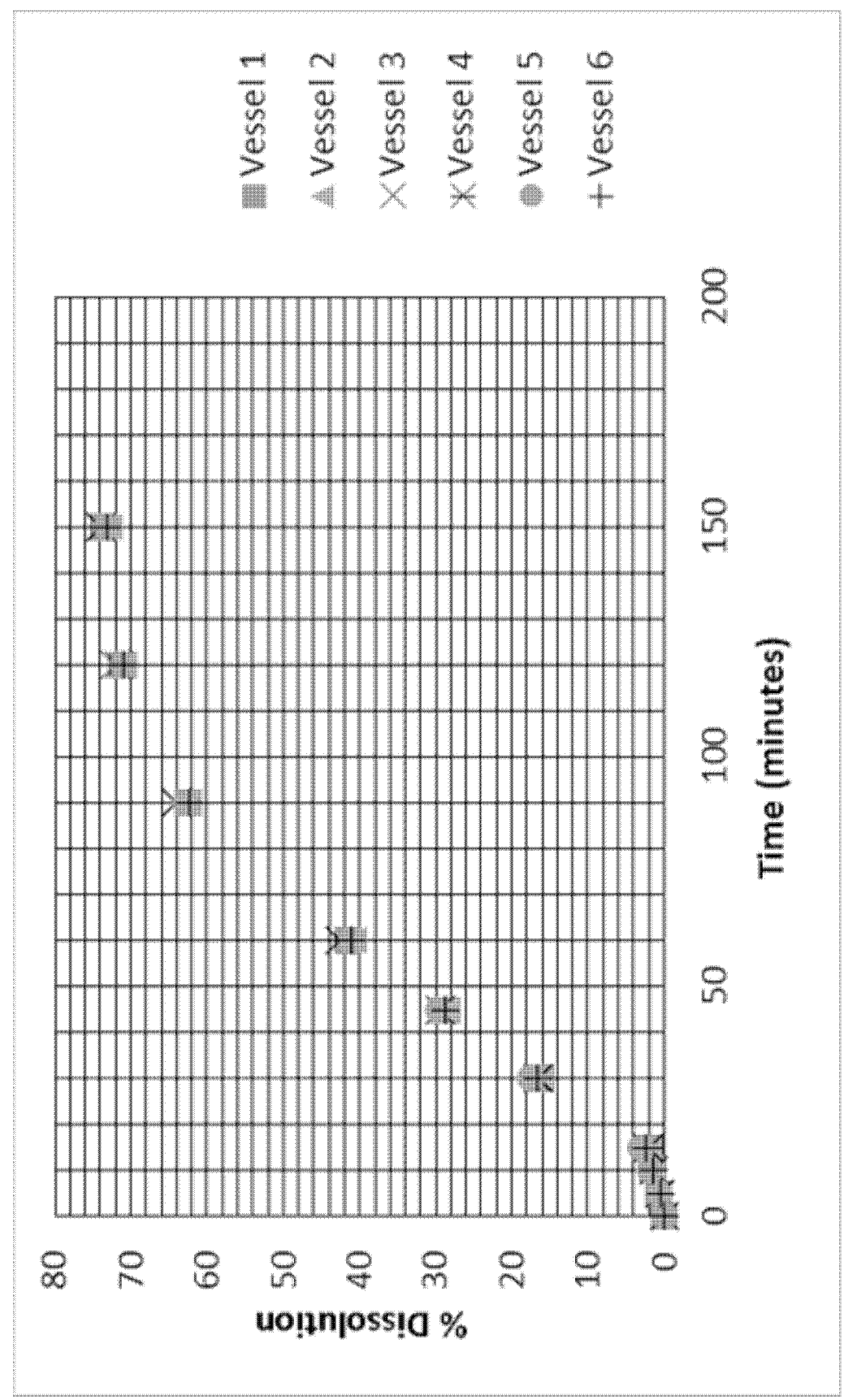
FIG. 1—% dissolution of pharmaceutically active binding polypeptide in The Pharmacopeial Dissolution Test (individual data points)

SEQ ID NO: 1—Polypeptide sequence of Q62E10
SEQ ID NO: 2—Polypeptide sequence of Q65F2
SEQ ID NO: 3—Polypeptide sequence of Q65F3
SEQ ID NO: 4—Polypeptide sequence of Q62F2
SEQ ID NO: 5—Polypeptide sequence of Q65G1
SEQ ID NO: 6—Polypeptide sequence of Q65H6
SEQ ID NO: 7—Polypeptide sequence of Q65F1
SEQ ID NO: 8—Polypeptide sequence of Q65D1
SEQ ID NO: 9—Polypeptide sequence of Q65C7
SEQ ID NO: 10—Polypeptide sequence of Q65D3
SEQ ID NO: 11—Polypeptide sequence of Q65B1
SEQ ID NO: 12—Polypeptide sequence of Q65F6
SEQ ID NO: 13—Polypeptide sequence of Q65F11
SEQ ID NO: 14—Polypeptide sequence of Q65E12
SEQ ID NO: 15—Polypeptide sequence of Q65C12
SEQ ID NO: 16—Polypeptide sequence of Q65A6
SEQ ID NO: 17—Polypeptide sequence of Q65A3
SEQ ID NO: 18—Polypeptide sequence of Q62F10
SEQ ID NO: 19—Polypeptide sequence of ID7F-EV
SEQ ID NO: 20—Polypeptide sequence of ID8F-EV
SEQ ID NO: 21—Polypeptide sequence of ID9F-EV
SEQ ID NO: 22—Polypeptide sequence of ID13F-EV
SEQ ID NO: 23—Polypeptide sequence of ID14F-EV
SEQ ID NO: 24—Polypeptide sequence of ID15F-EV
SEQ ID NO: 25—Polypeptide sequence of Q62E10-DVQLV
SEQ ID NO: 26—Polypeptide sequence of ID34F
SEQ ID NO: 27—Polypeptide sequence of ID37F
SEQ ID NO: 28—Polypeptide sequence of ID38F

DETAILED DESCRIPTION OF THE INVENTION

Release Profile

The release profile of a composition comprising a pharmaceutically active binding polypeptide is the quantity of pharmaceutically active binding polypeptide released from the composition, and is therefore free to bind its target, over time. The present application is concerned with the release profile of solid pharmaceutical compositions in the intestinal tract from the stomach to the rectum. Release profile may refer to that which is achieved in vivo during transit from the stomach to the rectum, or that which is achieved in an in vitro model of transit from the stomach to the rectum. Release profiles may be tested in vitro by dissolution testing using suitable dissolution apparatus, such as those described below. More suitably, the present application is concerned with the release profile of solid pharmaceutical compositions in the intestinal tract from the duodenum to the rectum and more suitably from the jejunum to the rectum.

The European Medicines Agency's "Guideline on quality of oral modified release products" under section "3.2. Setting specifications" states that at least two points should be included in a specification on in vitro dissolution of a gastro-resistant product: an early time point to exclude release in the acidic medium (less than 10% dissolved after 2 hours) and one to ensure that the majority of the active substance has been released in a (near) neutral medium.

"Delayed release" refers to the ability of a composition comprising a pharmaceutically active binding polypeptide to (a) protect the pharmaceutically active binding polypeptide from the external environment (e.g. acidic pH) and (b) not release any pharmaceutically active binding polypeptide to the external environment, until the composition reaches a desired region of the intestinal tract. Delayed release is achieved by virtue of a pH sensitive enteric coating. The longer the pH sensitive enteric coating maintains integrity, the longer the period of delayed release. The properties of the pH sensitive enteric coating may be adapted such that release may be additionally delayed (for example to ensure pharmaceutically active binding polypeptide is not released until the composition has passed the duodenum and has entered the jejunum). Alternatively, the properties of the pH sensitive enteric coating may be adapted such that release may be advanced (for example to ensure pharmaceutically active binding polypeptide is released only after exiting the stomach but while still inside the duodenum).

"Sustained release" refers to the ability of a composition comprising a pharmaceutically active binding polypeptide to release pharmaceutically active binding polypeptide into the external environment at a desired, ideally substantially constant rate, during transit through desired regions (or a desired region) of the intestinal tract.

A composition of the invention will suitably achieve both delayed release and sustained release.

There exist official in vitro tests of delayed and sustained release which are comprehensively defined in Pharmacopoeia. Tablet dissolution is a standardised method for measuring the rate of drug release from a dosage form. In vitro dissolution tests can be used to predict in vivo drug dissolution. Suitable in vitro dissolution tests are detailed below.

Delayed Release: Enteric Coating Release Profile

Measurement of Delayed Release: The Pharmacopeial Enteric Coating Test

A suitable and widely used standard method of testing an enteric coating is that provided by the European Pharmacopoeia 8.0 "2.9.3 Dissolution test for solid dosage forms" (which is harmonised with the corresponding texts of the United States Pharmacopeia and the Japanese Pharmacopoeia), referred to herein as the "Pharmacopeial Enteric Coating Test". This enteric coating test is carried out as follows.

1. The composition to be tested is added to 900 mL of 0.1 M HCl in USP2 apparatus (with band sinkers if presented in a capsule).

2. The composition and acid is stirred at 100 rpm for 2 hours.

The dissolution medium is sampled and analysed at 2 hours. Suitably the pharmaceutical composition releases less than 10% by weight of the pharmaceutically active binding polypeptide after 2 hours. More suitably the pharmaceutical composition releases less than 5% by weight of the pharmaceutically active binding polypeptide after 2 hours. More suitably the pharmaceutical composition releases less than 1% by weight of the pharmaceutically active binding polypeptide after 2 hours. More suitably the pharmaceutical composition releases no pharmaceutically active binding polypeptide after 2 hours.

Release of less than 10% by weight of the pharmaceutically active binding polypeptide after 2 hours indicates that the enteric coating provides adequate protection to the polypeptide preceding delivery to the desired region of the intestinal tract. A composition with this release profile achieves delayed release.

If desired, The Pharmacopeial Enteric Coating Test may be modified to continue to run for longer than 2 hours. This will allow analysis of the maximum time over which the pH sensitive enteric coating remains intact. When using small quantities of composition, accuracy of the test may be increased by reducing the volume of HCl used.

A pH sensitive enteric coating is said to be 'intact' when, based on visual inspection, the composition shows no signs of either disintegration or cracks that would allow the escape of the contents (as outlined in European Pharmacopoeia 8.0 2.9.3). Alternatively, a pH sensitive enteric coating can be said to be 'intact' when 1% or less, more suitably 0.5% or less or more suitably no pharmaceutically active binding polypeptide can be detected in the dissolution medium in which the composition is present. Suitably, the pH sensitive enteric coating remains intact for at least 2 hours, more suitably at least 3 hours, more suitably at least 4 hours, more suitably at least 5 hours, more suitably at least 6 hours during the Pharmacopeial Enteric Coating Test.

Sustained Release: Core Release Profile

Sustained release properties are suitably tested immediately after a composition has undergone testing for delayed release properties using The Pharmacopeial Enteric Coating Test detailed above. If this is the case, the composition should be sieved from the 0.1M HCl after delayed release test completion and washed with fresh 0.1M HCl, before finally transferring the composition to the dissolution media (phosphate buffer) described in the sustained release test described below.

Measurement of Sustained Release: The Pharmacopeial Dissolution Test

A suitable and widely used standard method of testing dissolution is that provided by the European Pharmacopoeia 8.0 "2.9.3 Dissolution test for solid dosage forms" (which is harmonised with the corresponding texts of the United States Pharmacopeia and the Japanese Pharmacopoeia). This dissolution test is referred to herein as the "Pharmacopeial Dissolution Test". This dissolution test is carried out as follows.

1. The composition to be tested is added to 900 mL of 0.05M pH 7.4 phosphate buffer in USP2 apparatus (with band sinkers if presented in a capsule).

2. The composition and buffer is stirred at 100 rpm for 2 hours.

3. The composition and buffer is then stirred at 200 rpm for 30 mins.

The dissolution medium may be sampled and analysed at 5, 10 15, 30, 45, 60, 90 and 120 minutes (during the 100 rpm stirring period) and at 150 minutes (during the 200 rpm stirring period).

Suitably, when assayed in the Pharmacopeial Dissolution Test, the pharmaceutical composition of the invention releases:

(i) 10-40% by weight of the pharmaceutically active binding polypeptide after 30 minutes,
(ii) 30-60% by weight of the pharmaceutically active binding polypeptide after 60 minutes and
(iii) 60% by weight or greater of the pharmaceutically active binding polypeptide after 120 minutes.

Figure 2:
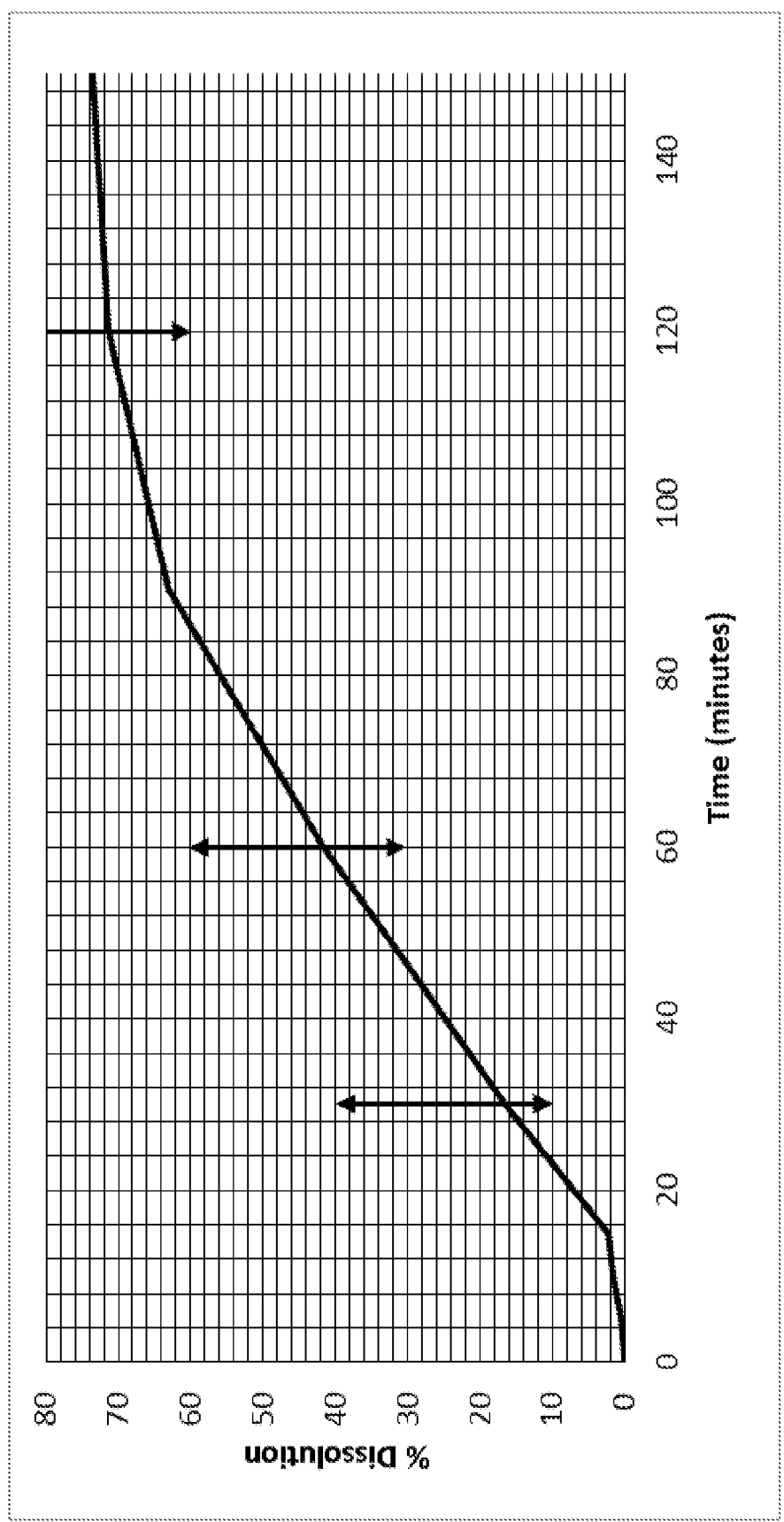
FIG. 2—% dissolution of pharmaceutically active binding polypeptide in The Pharmacopeial Dissolution Test (average of data points)

FIG. 2 illustrates the % dissolution profile achieved by the composition of Example 1 in the Pharmacopeial Dissolution Test. The dissolution ranges above are illustrated by arrows in FIG. 2.

More suitably, when assayed in the Pharmacopeial Dissolution Test, the pharmaceutical composition of the invention releases:

(i) 10-25% by weight of the pharmaceutically active binding polypeptide after 30 minutes,
(ii) 30-50% by weight of the pharmaceutically active binding polypeptide after 60 minutes and
(iii) 60% by weight or greater of the pharmaceutically active binding polypeptide after 120 minutes.

More suitably, when assayed in the Pharmacopeial Dissolution Test, the pharmaceutical composition of the invention releases:

(i) 13-20% by weight of the pharmaceutically active binding polypeptide after 30 minutes,
(ii) 35-45% by weight of the pharmaceutically active binding polypeptide after 60 minutes and
(iii) 65% by weight or greater of the pharmaceutically active binding polypeptide after 120 minutes.

Delayed and Sustained Release: Joint Enteric Coating and Core Release Profile

The Dynamic Dissolution Test

Alternatively, or in addition to the Pharmacopeial tests described above, a suitable method of jointly testing an enteric coating and core release profile is referred to herein as "The Dynamic Dissolution Test".

Figure 3:
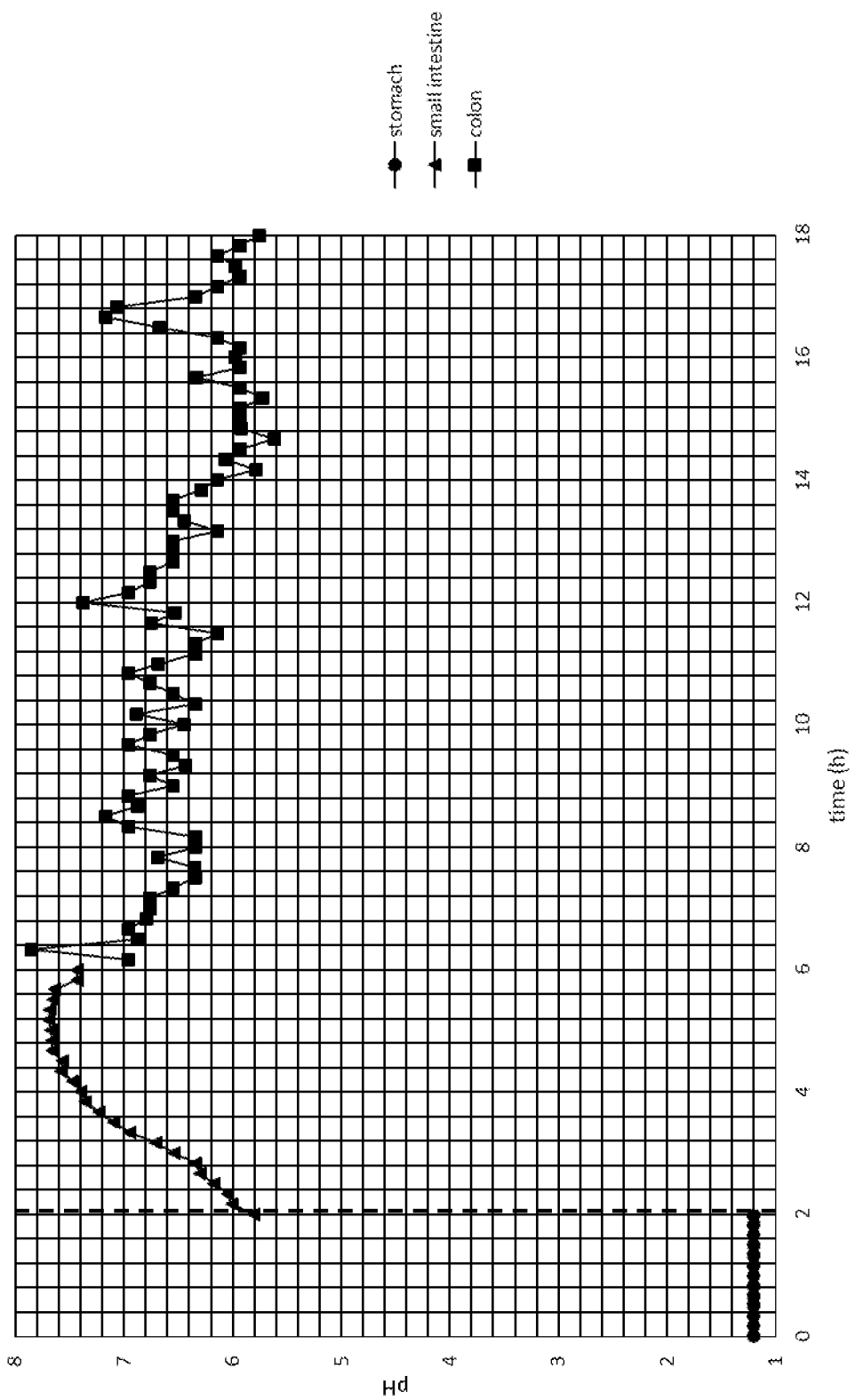
FIG. 3—Simulated stomach and intestinal pH profile for fasting conditions used in The Dynamic Dissolution Test FIG. 4—% dissolution of pharmaceutically active binding polypeptide in The Dynamic Dissolution Test (Batch A)

FIG. 3 illustrates the simulated pH profile for fasting conditions which is used in The Dynamic Dissolution Test. Further information on this test is available primarily in Garbacz et al 2014 and also in Fadda et al 2009, Merchant et al 2014, and Goyanes et al 2015. This test is carried out as follows.

1. The composition to be tested is added to 900 mL of 0.1M HCl in USP2 apparatus.

2. The composition and acid is stirred at 50 rpm for 2 hours.

This 2 hour period in 0.1M HCl is denoted by the region of FIG. 3 preceding the dotted line.

The dissolution medium is sampled and analysed at 2 hours. Suitably the pharmaceutical composition releases less than 10% by weight of the pharmaceutically active binding polypeptide after 2 hours. More suitably the pharmaceutical composition releases less than 5% by weight of the pharmaceutically active binding polypeptide after 2 hours. More suitably the pharmaceutical composition releases less than 1% by weight of the pharmaceutically active binding polypeptide after 2 hours. More suitably the pharmaceutical composition releases no pharmaceutically active binding polypeptide after 2 hours.

Release of less than 10% by weight of the pharmaceutically active binding polypeptide after 2 hours indicates that the enteric coating provides adequate protection to the polypeptide preceding delivery to the desired region of the intestinal tract. A composition with this release profile achieves delayed release.

The next stage of this test ascertains the dissolution of a composition during transit through the varying pH profile existent along the gastrointestinal tract. FIG. 3 (curve following the dotted line) illustrates the simulated pH profile for fasting conditions which is used. This stage of the test is carried out as follows.

1. The composition being tested is transferred to 900 mL of pH 5.79 Hanks hydrogen carbonate buffer (details in Table 1 below) in USP2 apparatus (the moment of transfer to Hanks buffer is denoted by the dotted line in FIG. 3).

2. The composition and buffer is stirred at 50 rpm for 16 hours over which time the pH of the dissolution medium is varied according to FIG. 3. Variation of the dissolution medium pH may be varied by exposure to gaseous carbon dioxide (to lower pH) or gaseous nitrogen (to raise pH). The pH profile simulates a median pH profile of small bowel passage as well as model pH profile of colonic transit, during fasting.

3. The composition and buffer is then stirred at 200 rpm for 2 hours.

TABLE 1

| Amount for 1 L (g) | Compound | CAS Number |
|---|---|---|
| 0.06 | Potassium dihydrogen phosphate | 7778-77-0 |
| 8.00 | Sodium chloride | 7647-14-5 |
| 0.03 | Sodium dihydrogen phosphate dihydrate | 13472-35-0 |
| 0.04 | Calcium chloride | 10035-04-8 |
| 0.40 | Potassium chloride | 7447-40-7 |
| 0.20 | Magnesium sulfate | 10034-99-8 |
| 0.35 | Sodium hydrogen carbonate | 144-55-8 |

Samples may be taken every 10 minutes for the duration of the test for analysis of the quantity of released pharmaceutically active binding polypeptide.

Suitably the start of release of the pharmaceutically active binding polypeptide occurs between 90 to 210 minutes from addition of the composition to Hanks buffer. 'Start of release' as used herein refers to the first point in the Dynamic Dissolution Test after addition to Hanks buffer at which greater than 1% of pharmaceutically active binding polypeptide is released from the core.

Suitably, when assayed in the Dynamic Dissolution Test, the pharmaceutical composition releases:
(i) 10-30% by weight of the pharmaceutically active binding polypeptide after 60 minutes from start of release,
(ii) 40-70% by weight of the pharmaceutically active binding polypeptide after 120 minutes from start of release and
(iii) 60% by weight or greater of the pharmaceutically active binding polypeptide after 180 minutes from start of release.

Suitably, when assayed in the Dynamic Dissolution Test, the pharmaceutical composition releases:
(i) 10-30% by weight of the pharmaceutically active binding polypeptide after 60 minutes from start of release,
(ii) 40-60% by weight of the pharmaceutically active binding polypeptide after 120 minutes from start of release and
(iii) 60% by weight or greater of the pharmaceutically active binding polypeptide after 180 minutes from start of release.

More suitably, when assayed in the Dynamic Dissolution Test, the pharmaceutical composition releases:
(i) 12-25% by weight of the pharmaceutically active binding polypeptide after 60 minutes from start of release,
(ii) 45-58% by weight of the pharmaceutically active binding polypeptide after 120 minutes from start of release and
(iii) 65% by weight or greater of the pharmaceutically active binding polypeptide after 180 minutes from start of release.

On occasion, a small premature release of polypeptide can occur immediately on addition to Hanks buffer, followed by substantial release commencing shortly after. "Start of substantial release" can therefore be defined as the point at which greater than 1% of the pharmaceutically active binding polypeptide has been released and wherein a progressive increase in the amount of released pharmaceutically active binding polypeptide occurs at each of the time points 10, 20 and 30 minutes thereafter.

Suitably, when assayed in the Dynamic Dissolution Test, the pharmaceutical composition releases:
(i) 10-30% by weight of the pharmaceutically active binding polypeptide after 60 minutes from start of substantial release,
(ii) 40-70% by weight of the pharmaceutically active binding polypeptide after 120 minutes from start of substantial release and
(iii) 60% by weight or greater of the pharmaceutically active binding polypeptide after 180 minutes from start of substantial release.

Measurement of the Quantity of Released Pharmaceutically Active Binding Polypeptide (% Dissolution)

Measurement of % dissolution of pharmaceutically active binding polypeptide in the tests above may for example be performed by UV or HPLC analysis of the dissolution medium. Suitably, in the tests described above, measurement of % dissolution of pharmaceutically active binding polypeptide is performed by UV analysis of the dissolution medium. Suitably a UV path length of 10 mm and a spectrometer wavelength of 279 nm is used. The absorbance of standard solutions containing known quantities of polypeptide are measured to produce a standard curve, from which the % of released pharmaceutically active binding polypeptide is then ascertained. Alternatively, it may be assumed that this curve is linear and a single point determination of the standard may be made.

Without being bound by theory, it is believed that a gelling phenomenon caused on contact of the pharmaceutical composition with an aqueous environment contributes to the sustained release profile of the pharmaceutically active binding polypeptide incorporated in the composition of the invention, such that the polypeptide is released into the dissolution medium or in vivo environment at a slower and more consistent rate than would be expected from a compound with high water solubility.

Intestinal Transit Times

Approximate human intestinal transit times (hours) in the fasting state through each region of the small intestine are as follows:

| | |
|---|---|
| Through duodenum | 0.3 |
| Through jejunum | 1.7 |
| Through ileum | 1.3 |

Transit times in the fed state are similar to those above. In light of these transit times, a composition with a pH sensitive enteric coating formulated such that polypeptide starts to be released after approximately 18 minutes from entering the higher pH buffer environment in vitro may be expected to first release polypeptide in vivo in the jejunum. Similarly, a composition with a pH sensitive enteric coating formulated such that polypeptide starts to be released after approximately 120 minutes from entering the higher pH buffer environment in vitro may be expected to first release polypeptide in vivo in the ileum. Release would continue and then plateau while the composition passes through the remaining lower regions of the intestinal tract.

Tablet Components

Pharmaceutically Active Binding Polypeptides

Polypeptides are organic polymers consisting of a number of amino acid residues bonded together in a chain. As used herein, 'polypeptide' is used interchangeably with 'protein' and 'peptide'. Polypeptides are said to be binding polypeptides when they contain one or more stretches of amino acid residues which form an antigen-binding site, capable of binding to an epitope on a target antigen with an affinity (suitably expressed as a Kd value, a Ka value, a kon-rate and/or a koff-rate, as further described herein). 'Binding polypeptide' and 'antigen-binding polypeptide' are used synonymously herein. A binding polypeptide is pharmaceutically active if the binding polypeptide is capable of exerting a beneficial pharmacological effect upon administration to a subject. Suitably a polypeptide is a pharmaceutically active binding polypeptide such that the polypeptide binds to, and more suitably antagonises or neutralises, a biological target (typically a protein such as a receptor, ion channel, enzyme, structural protein or cytokine). In some embodiments the pharmaceutically active binding polypeptide may agonise the biological target (such as a receptor). Pharmaceutically active binding polypeptides may include polypeptides such as antibodies (which are further described below), antibodies modified to comprise additional binding regions, antibody mimetics and antigen-binding antibody fragments (which are further described below). Further pharmaceutically active binding polypeptides may include DARPins (Binz et al. Journal of Molecular Biology 332(2):489-503), Affimers™, Fynomers™, Centyrins, Nanofitins® and cyclic peptides.

A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains ("ICVDs"). The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al., 1991, herein incorporated by reference in its entirety). In a conventional antibody, each VHC and VLC is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulfide bonds, and the heavy chains similarity connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans 2013, Hamers-Casterman et al., 1993, Muyldermans et al., 1994, herein incorporated by reference in their entirety).

An antigen-binding antibody fragment (or "antibody fragment", "immunoglobulin fragment" or "antigen-binding fragment") as used herein refers to a portion of an antibody that specifically binds to a target (e.g. a molecule in which one or more immunoglobulin chains is not full length, but which specifically binds to a target). Examples of fragments encompassed within the term antigen-binding antibody fragment include:

(i) a Fab fragment (a monovalent fragment consisting of the VLC, VHC, CL and CH1 domains);

(ii) a F(ab')2 fragment (a bivalent fragment comprising two Fab fragments linked by a disulfide bridge at the hinge region);

(iii) a Fd fragment (consisting of the VHC and CH1 domains);

(iv) a Fv fragment (consisting of the VLC and VHC domains of a single arm of an antibody);

(v) an scFv fragment (consisting of VLC and VHC domains joined, using recombinant methods, by a synthetic linker that enables them to be made as a single protein chain in which the VLC and VHC regions pair to form monovalent molecules);

(vi) a VH (an immunoglobulin chain variable domain consisting of a VHC domain (Ward et al., 1989));

(vii) a VL (an immunoglobulin chain variable domain consisting of a VLC domain);

(viii) a V-NAR (an immunoglobulin chain variable domain consisting of a VHC domain from chondrichthyes IgNAR (Roux et al., 1998 and Griffiths et al., 2013, herein incorporated by reference in their entirety))

(ix) a VHH.

The total number of amino acid residues in a pharmaceutically active binding polypeptide may be in the region of 50-3000, more suitably 100-1500, more suitably 100-1000, more suitably 100-500, more suitably 100-200. The total number of amino acid residues in a VHH or VH may be in the region of 110-140, is suitably 112-130, and more suitably 115-125.

The examples provided herein relate to compositions comprising immunoglobulin chain variable domains per se. The principles of the invention disclosed herein are, however, equally applicable to a composition according to the invention comprising any pharmaceutically active binding polypeptide. For example, the anti-TNF-alpha immunoglobulin chain variable domains featured in the examples disclosed herein may be incorporated into a polypeptide such as a full length antibody. Such an approach is demonstrated by McCoy et al., 2014, who provide an anti-HIV VHH engineered as a fusion with a human Fc region (including hinge, CH2 and CH3 domains), expressed as a dimer construct.

Suitably, the pharmaceutically active binding polypeptide consists of an immunoglobulin chain variable domain. Suitably, the pharmaceutically active binding polypeptide is an antibody or an antibody fragment. Suitably the antibody fragment is a VHH, a VH, a VL, a V-NAR, a Fab fragment, a VL or a F(ab')2 fragment (such as a VHH or VH, most suitably a VHH).

Suitably the molecular weight of the pharmaceutically active binding polypeptide is 1-200 kD. More suitably 5-200 kDa, more suitably 10-200 kDa, more suitably 10-180 kDa, more suitably 10-150 kDa, more suitably 10-100 kDa, more suitably 10-50 kDa, more suitably 10-20 kDa, more suitably 12-15 kDa, more suitably about 13 kDa.

Suitably the pharmaceutically active binding polypeptide has an aqueous solubility of greater than 1 mg/mL, more suitably greater than 5 mg/mL, more suitably greater than 10 mg/mL, more suitably greater than 15 mg/mL, more suitably greater than 20 mg/mL, more suitably greater than 25 mg/mL, more suitably greater than 30 mg/mL.

Suitably the isoelectric point of the pharmaceutically active binding polypeptide is 6-8, more suitably 6.5-7.5, more suitably 6.7-6.9, more suitably about 6.8.

SEQ ID Nos: 1 to 28 are polypeptide sequences of specific ICVDs which are exemplary pharmaceutically active binding polypeptides according to the invention. Suitably the pharmaceutically active binding polypeptide comprises or more suitably consists of any one or more of SEQ ID Nos: 1 to 28.

Suitably the pharmaceutically active binding polypeptide is for local delivery to a region of the intestinal tract. Suitably the pharmaceutically active binding polypeptide is for local therapeutic effect. "Local therapeutic effect" is defined as a beneficial biological impact which only takes place, or is only appreciable, in the region to which a pharmaceutically active binding polypeptide was first delivered. Local therapeutic effect excludes systemic effects (beneficial or otherwise). For example, a pharmaceutically active binding polypeptide which targets TNF-alpha, when delivered in a composition of the invention, suitably binds to and neutralises the effects of TNF-alpha present in the region(s) of the intestinal tract in which it was first released. This pharmaceutically active binding polypeptide does not, however, significantly bind to significant quantities of TNF-alpha in other regions of the body and therefore does not have a significant systemic impact.

The pharmaceutical composition of the invention provides protection to a pharmaceutically active binding polypeptide during transit through the stomach and suitably also the duodenum, until pharmaceutically active binding polypeptide is released in target regions of the intestinal tract. Accordingly, particularly suitable pharmaceutically active binding polypeptides are those which are substantially inactivated when exposed to the stomach and/or duodenum and which are therefore protected from inactivation by the pH sensitive enteric coating of the composition of the invention.

It is possible that a crude sample of polypeptide may contain impurities (such as inactive polypeptide) such that only a proportion of a polypeptide sample will be pharmaceutically active binding polypeptide.

The pharmaceutically active binding polypeptide can be in the form of a pharmaceutically acceptable salt. Suitably the pharmaceutically active binding polypeptide is not insulin. Suitably the pharmaceutically active binding polypeptide is intra-granular.

Pharmaceutically active binding polypeptides can be obtained and manipulated using the techniques disclosed for example in Green and Sambrook 2012. For example, immunoglobulin chain variable domains may be obtained by preparing a nucleic acid encoding an immunoglobulin chain variable domain using techniques for nucleic acid synthesis, followed by expression of the nucleic acid thus obtained.

Specificity and Affinity

Specificity refers to the number of different types of antigens or antigenic determinants to which a particular antigen-binding polypeptide can bind. The specificity of an antigen-binding polypeptide is the ability of the antigen-binding polypeptide to recognise a particular antigen as a unique molecular entity and distinguish it from another.

Affinity, represented by the equilibrium constant for the dissociation of an antigen with an antigen-binding polypeptide (Kd), is a measure of the binding strength between an antigenic determinant and an antigen-binding site on the antigen-binding polypeptide: the lesser the value of the Kd, the stronger the binding strength between an antigenic determinant and the antigen-binding polypeptide (alternatively, the affinity can also be expressed as the affinity constant (Ka), which is 1/Kd). Affinity can be determined by known methods, depending on the specific antigen of interest.

Suitably, a pharmaceutically active binding polypeptide will bind with a dissociation constant (Kd) of at least $1\times10^{-6}$ M, more suitably at least $1\times10^{-7}$ M, more suitably at least $1\times10^{-8}$ M, more suitably at least $1\times10^{-9}$ M.

Any Kd value less than $10^{-6}$ is considered to indicate binding. Specific binding of pharmaceutically active binding polypeptide to an antigen or antigenic determinant can be determined in any suitable known manner, including, for example, Scatchard analysis and/or competitive binding assays, such as radioimmunoassays (RIA), enzyme immunoassays (EIA) and sandwich competition assays, and the different variants thereof known in the art.

An anti-target polypeptide, a polypeptide which interacts with a target, or a polypeptide against a target, are all effectively polypeptides which bind to a target. A polypeptide may bind to a linear or conformational epitope.

Suitably the pharmaceutically active antigen binding polypeptide binds to a target in the intestinal tract, such as a target in one or more regions of the intestinal tract, such as an interleukin (such as IL-1, IL-1ra, IL-4, IL-5, IL-6, IL-7, IL-8, IL-9, IL-10, IL-11, IL-12, IL-13, IL-15, IL-17, IL-18 and IL-23), an interleukin receptor (such as IL-6R and IL-7R), a transcription factor (such as NF-kB), a cytokine (such as TNF-alpha, IFN-gamma TGF-beta and TSLP), a transmembrane protein (such as gp130 and CD3), a surface glycoprotein (such as CD4, CD20, CD40), a soluble protein (such as CD40L), an integrin (such as a4b7 and Alpha-Ebeta7), an adhesion molecule (such as MAdCAM), a chemokine (such as IP10 and CCL20), a chemokine receptor (such as CCR2 and CCR9), an inhibitory protein (such as SMAD7), a kinase (such as JAK3), a G protein-coupled receptor (such as sphingosine-1-P receptor) and products of gastrointestinal pathogens.

Linkers and Multimers

A pharmaceutically active binding polypeptide may be a construct comprising multiple polypeptides and therefore may suitably be multivalent. Such a construct may comprise at least two identical polypeptides. Alternatively, a construct may comprise at least two polypeptides which are different. Constructs can be multivalent and/or multispecific. A multivalent construct (such as a bivalent construct) comprises two or more binding polypeptides and therefore presents two or more sites at which attachment to one or more antigens can occur. A multispecific construct (such as a bispecific construct) comprises two or more different binding polypeptides which present two or more sites at which either (a) attachment to two or more different antigens can occur or (b) attachment to two or more different epitopes on the same antigen can occur. A multispecific construct is multivalent.

The polypeptides in the construct can be linked to each other directly (i.e. without use of a linker) or via a linker. Suitably, the linker is a protease-labile or a non-protease-labile linker. The linker is suitably a polypeptide and will be selected so as to allow binding of the polypeptides to their epitopes. If used for therapeutic purposes, the linker is suitably non-immunogenic in the subject to which the polypeptides are administered. Suitably the polypeptides are all connected by non-protease-labile linkers. Suitably the non-protease-labile linkers are of the format $(G_4S)_x$. Suitably x is 1 to 10, most suitably x is 6. Suitably the protease-labile linker is of the format $[-(G_aS)_x-B-(G_bS)_y-]_z$ wherein a is 1 to 10; b is 1 to 10; x is 1 to 10; y is 1 to 10, z is 1 to 10 and B is K or R. Suitably a is 2 to 5, more suitably a is 4. Suitably b is 2 to 5, more suitably b is 4. Suitably x is 1 to 5, more suitably x is 1. Suitably y is 1 to 5, more suitably y is 1. Suitably z is 1 to 3, more suitably z is 1. Suitably B is K. Capital lettering in the passage above refers to the single letter amino acid code.

pH Sensitive Enteric Coatings

The pharmaceutical composition of the invention is provided with a pH sensitive enteric coating. Materials used for enteric coatings include fatty acids, waxes, shellac, plastics, and plant fibers. Suitably the pH sensitive enteric coating releases pharmaceutically active binding polypeptide when exposed to a region of the intestinal tract. Suitably the region of the intestinal tract is a region of the small and/or large intestine such as a region selected from at least one of the duodenum, jejunum, ileum, cecum, colon, rectum and anal canal. More suitably the region is selected from at least one of the duodenum, jejunum and ileum.

The thickness of the pH sensitive enteric coating is selected such that the coating remains intact for the desired period of time during transit through the gastrointestinal tract and in particular for the desired period of time following exposure to a pH which results in dissolution of the coat. Suitably the thickness of the pH sensitive enteric coating (e.g. a pH sensitive enteric coating comprising poly(methacrylic acid-co-methyl methacrylate) 1:1 is 10-300 um, such as 50-200 um, such as 70-170 um, such as 100-170 um.

Suitably, the quantity of pH sensitive enteric coating used in a composition of the invention is present at 10-30%, more suitably 15-26%, more suitably 17-23%, more suitably 18-22%, more suitably about 20% w/w of the composition as a whole. Suitably these quantities are in the context of a 3 mm diameter compressed core.

Suitably the quantity of pH sensitive enteric coating used in a composition of the invention is present at 15-35%, more suitably 20-30%, more suitably 22-28%, more suitably 24-26%, more suitably about 25% w/w of the core. Suitably these quantities are in the context of a 3 mm diameter compressed core.

Alternatively, the quantity of pH sensitive enteric coating used in a composition of the invention may be defined by the % weight gained by the compressed core (or suitably the sub-coated compressed core) upon addition of a pH sensitive enteric coating. In the Examples it is demonstrated that a weight gain of 25% w/w of pH sensitive enteric coating resulted in the coating coming off after approximately 2 hours during the Dynamic Dissolution Test and that a weight gain of 17% w/w of pH sensitive enteric coating resulted in the coating coming off after approximately 90 minutes during the Dynamic Dissolution Test. Therefore a range of 14%-30%, or more suitably 17%-27%, or more suitably 20-27% weight gained upon coating with pH sensitive enteric coating should provide an optimal coating for dissolution in the small intestine. Furthermore, more specifically and if desired, 17%-20% weight gained upon coating with pH sensitive enteric coating should provide an optimal coating for dissolution in the duodenum or 20%-27% weight gained upon coating with pH sensitive enteric coating should provide an optimal coating for dissolution in the ileum. Suitably these quantities are in the context of a 3 mm diameter compressed core.

If a compressed core has a cylindrical profile (such as a cylindrical minitablet), thickness measurements are suitably obtained by slicing the mini-tablets both axially and radially (ignoring the thickness of the coating on the corners of the tablets).

pH Sensitive Enteric Polymer Coat

The pH sensitive enteric coating may comprise a pH sensitive enteric polymer coat. A pH sensitive enteric polymer coat is a polymer which is included in the pH sensitive enteric coat and which acts as a barrier to protect the polypeptide from the low pH of the stomach and suitably also the duodenum. A pH sensitive enteric polymer coat is insoluble at the highly acidic pH found in the stomach, but dissolves rapidly at a less acidic pH. Thus, suitably, the pH sensitive enteric polymer coat will not dissolve in the acidic juices of the stomach (pH 1.5-4), but will do so in the higher pH environment present in the small intestine (pH above 6) or in the colon (pH above 7.0). The pH sensitive enteric polymer coat is selected such that the polypeptide will start to be released at about the time that the dosage reaches the small intestine, particularly the duodenum, jejunum and ileum; most suitably when the dosage reaches the jejunum.

Suitably the pH sensitive enteric polymer coat does not dissolve until after 2 hours or longer exposure (suitably at least 6 hours, more suitably 2-4 hours, more suitably 2-3 hours) to a pH of 0.5-3.5, more suitably 0.6-3.0, more suitably 0.7-2.5, more suitably 0.8-2.0, more suitably 0.9-1.5, more suitably about or exactly 1. The skilled person will appreciate that proton pump inhibitors, H2 inhibitors and acid neutralisers may raise stomach pH to approximately 4 or even greater and therefore a pH sensitive enteric polymer coat which dissolves at a higher pH may appropriately be used in a composition of the invention if taken simultaneously with proton pump inhibitors. Similarly, the skilled person will appreciate that a subject suffering from e.g. achlorhydria will have a raised stomach pH (of greater than 5) and therefore a pH sensitive enteric polymer coat which dissolves at a higher pH may appropriately be used in a composition of the invention if administered to a subject suffering from such a condition.

Suitably the pH sensitive enteric polymer coat comprises one or more of: methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. More suitably the pH sensitive enteric polymer coat comprises or consists of an anionic copolymer based on methacrylic acid and methyl methacrylate. More suitably the pH sensitive enteric polymer coat comprises or consists of poly(methacrylic acid-co-methyl methacrylate) 1:1 (e.g. Eudragit L100/L12.5) or poly(methacrylic acid-co-ethyl acrylate) 1:1 (e.g. Eudragit L100-55/L30-D55); most suitably poly(methacrylic acid-co-methyl methacrylate) 1:1.

The quantity of pH sensitive enteric polymer coat used in a composition of the invention may be expressed as a percentage w/w of the pH sensitive enteric coating (i.e. the total solids of the pH sensitive enteric coating). Suitably the pH sensitive enteric polymer coat is present at 40-70%, more suitably 55-65% by weight relative to the pH sensitive enteric coating.

The quantity of pH sensitive enteric polymer coat used in a composition of the invention may also be expressed as a percentage w/w of the composition as a whole. Suitably, the quantity of pH sensitive enteric polymer coat used in a composition of the invention is present at 10-30%, more suitably about 12% w/w of the composition as a whole.

If an entirely aqueous coating method is used to produce the composition of the invention as opposed to a mixed aqueous and organic solvent method then, in order to achieve an equivalent release profile, the quantity of pH sensitive enteric polymer coating should be increased relative to that used in an aqueous and organic solvent method.

Further Possible Components of the pH Sensitive Enteric Coat

Suitably the pH sensitive enteric coating comprises or consists of a pH sensitive enteric polymer coat optionally together with one or more of a plasticiser, an anti-tacking agent and a surfactant. More suitably the pH sensitive enteric coating consists of a pH sensitive enteric polymer coat, a plasticiser, an anti-tacking agent and a surfactant.

Suitably the pH sensitive enteric coating comprises a plasticiser wherein the plasticiser is triethyl citrate, the anti-tacking agent is talc and/or the surfactant is sodium lauryl sulphate. Suitably the plasticiser is present at 5-20% by weight relative to the pH sensitive enteric coating and/or the anti-tacking agent is present at 20-40% by weight relative to the pH sensitive enteric coating and/or the surfactant is present at 0.05-0.5% by weight relative to the pH sensitive enteric coating.

Suitably the pH sensitive enteric coating comprises, essentially consists of, or consists of the following: 50-70% one or more pH sensitive enteric polymer coat, 7-17% one or more plasticisers, 20-40% one or more anti-tacking agents and 0.05-0.2% surfactant; all by weight relative to the weight of the pH sensitive enteric coating.

Suitably a composition of the invention may comprise a sub-coating between the compressed core and the pH sensitive enteric coating. Such a sub-coating may improve adherence of the pH sensitive enteric coating to the core. Suitably the sub-coating comprises or consists of hydroxypropylmethylcellulose.

Excipients

The pharmaceutical composition of the invention suitably comprises at least one excipient. Suitably the at least one excipient is selected from one or more of: (i) one or more compression aids, (ii) one or more disintegrants, (iii) one or more lubricants, (iv) one or more glidants, (v) one or more diluents and (vi) one or more binders. These excipients are detailed as follows. % values expressed below are expressed as % weight of the compressed core.

Compression Aids

Compression aids serve to bind the components of the core together giving form and mechanical strength. Suitably the one or more compression aids are intra-granular and extra-granular.

Suitably the composition of the invention comprises one or more compression aids. Suitably the one or more compression aids is selected from the list consisting of synthetic polymers such as crospovidone, saccharides such as sucrose, glucose, lactose and fructose, sugar alcohols such as mannitol, xylitol, maltitol, erythritol, sorbitol, water-soluble polysaccharides such as celluloses such as crystalline cellulose, microcrystalline cellulose, powdered cellulose, hydroxypropylcellulose and methyl cellulose, starches, synthetic polymers such as polyvinylpyrrolidone, sodium starch glycolate, crospovidone and inorganic compounds such as calcium carbonate.

Suitably the one or more compression aids is present at 20-55%, such as 30-40% by weight relative to the weight of the core.

It has been found that, surprisingly, mannitol improves the thermal stability of the pharmaceutically active binding polypeptide detailed in Example 1 (see Example 6). Suitably therefore, the one or more compression aids is mannitol.

Binders

Binders are similar in function to compression aids. Suitably the core of the composition of the invention comprises one or more binders. Suitably the one or more binders are intra-granular and extra-granular. Suitably the one or more binders is selected from the list consisting of acacia, alginic acid, ammonio methacrylate copolymer, ammonio methacrylate copolymer dispersion, carbomer copolymer, carbomer homopolymer, carbomer interpolymer, carboxymethylcellulose sodium, microcrystalline cellulose, copovidone, sucrose, dextrin, ethylcellulose, gelatin, glucose, guar gum, low-substituted hydroxypropyl cellulose, hypromellose, hydromellose acetate succinate, maltodextrin, maltose, methylcellulose, polyethylene oxide, povidone, starch such as corn starch; potato starch; pregelatinized starch; tapioca starch; wheat starch.

Suitably the one or more binders are present at 20-55%, such as 30-40% by weight relative to the weight of the core.

Suitably the one or more binders and compression aids are present at 20-55%, such as 30-40% by weight relative to the weight of the core.

Disintegrants

Disintegrants serve to aid dispersion of the core in the gastrointestinal tract, assisting to release the pharmaceutically active binding polypeptide and increasing the surface area for dissolution. Disintegrants include super disintegrants. Suitably the core of the composition of the invention comprises one or more disintegrants. Suitably the one or more disintegrants are extragranular.

It is possible for disintegrants to counteract the effect of polypeptide gelling and as such disintegrants may be used to finely modulate the release profile of a composition of the invention.

Suitably the one or more disintegrants is selected from the list consisting of carboxymethyl cellulose, sodium carboxymethyl cellulose, croscarmellose sodium, cellulose such as low substitution degree hydroxypropylcellulose, starch such as sodium carboxymethyl starch, hydroxypropyl starch, rice starch, wheat starch, potato starch, maize starch, partly pregelatinized starch. Suitably the disintegrant is croscarmellose sodium. Suitably the one or more disintegrants is present at 2-6%, such as about 4% by weight relative to the weight of the core.

It has been found that, surprisingly, croscarmellose sodium improves the thermal stability of the pharmaceutically active binding polypeptide detailed in Example 1 (see 'D', Example 6). Suitably therefore, the one or more disintegrants is croscarmellose sodium.

Glidants

Glidants improve the flow of powders during tablet manufacturing by reducing friction and adhesion between particles. The core of the composition of the invention may comprise one or more glidants. If present, the glidants may be intra-granular or extra-granular. Suitably the one or more glidants, if present, is selected from the list consisting of calcium silicate, magnesium silicate, colloidal silicon dioxide and talc. Most suitably the one or more glidants, if present, is colloidal silicon dioxide. Suitably the one or more glidants, if present, is present at 0.1-1.0%, more suitably about 0.5% by weight relative to the weight of the core.

Lubricants

Lubricants have a similar action to glidants. Lubricants are added primarily to prevent sticking of the punches in the die during tabletting. They may also slow disintegration and dissolution. Suitably the core of the composition of the invention comprises one or more lubricants. Suitably the lubricants are intra-granular and extra-granular. Suitably the one or more lubricants is selected from the list consisting of glyceryl behenate, a stearic acid salt such as calcium stearate; magnesium stearate; zinc stearate, mineral oil, polyethylene glycol, sodium lauryl sulfate, sodium stearyl fumarate, starch such as corn starch; potato starch; pregelatinized starch; tapioca starch; wheat starch, stearic acid, talc, vegetable oil and zinc stearate.

Suitably the core comprises one or more lubricants wherein the one or more lubricants is present at 0.1-2%, such as about 1% by weight relative to the weight of the core.

It has been found that, surprisingly, magnesium stearate improves the thermal stability of the pharmaceutically active binding polypeptide detailed in Example 1 (see 'E', Example 6). Suitably therefore, the one or more lubricants is magnesium stearate.

Other Components

The advantageous release profiles of compositions of the invention can be achieved without addition of substances which conventionally delay the release of pharmaceutically active binding polypeptide, or protect pharmaceutically active binding polypeptide, such as hydrogels. Hydrogels are three-dimensional mesh like networks containing hydrophilic polymers that imbibe substantial quantities of water and form a gel like matrix as a result of physical or chemical cross linking of individual polymer chains. Suitably the composition of the invention comprises less than 1%, more suitably less than 0.5%, more suitably less than 0.1% by weight hydrogels, more suitably the composition of the invention comprises no hydrogels. Furthermore, the advantageous release profiles of compositions of the invention may be achieved without including alginates, hydroxypropyl methylcellulose (HPMC) and/or copolymers based on methacrylic acid and methyl methacrylate in the compressed core of the composition. The advantageous release profiles of compositions of the invention are furthermore suitably achieved without addition of sustained release coatings (e.g. a coat permitting diffusion of active agent, which may be positioned between the pH sensitive enteric coat and the compressed core). Similarly, the compositions of the invention suitably do not comprise any one or more of the following components which can be added to formulations to achieve absorption of the active ingredient: penetration/permeability enhancers (including cell penetrating peptides or membrane modifying substances); carrier systems (including nanoparticles, cyclodextrins, polymeric carriers or lipid based systems); mucous modifying, adhesive or penetrating excipients; or sugar micro needles.

Presentation Forms and Structure

The pharmaceutical compositions of the invention may be presented in a variety of forms. These include solid oral dosage forms comprising pH sensitive enteric coatings and compressed cores such as tablets or mini-tablets.

Mini-tablets may be round, cylindrical tablets or disc-like in shape. Mini-tablets are suitably 1 to 5 mm in diameter, more suitably 1-4 mm in diameter, more suitably 1-3 mm in diameter, more suitably 2-3 mm in diameter, more suitably about 3 mm in diameter, more suitably about 2 mm in diameter. Mini-tablets are typically produced by compression. They provide a smooth substrate for enteric coating using e.g. either conventional perforated coating pans or fluid-bed apparatus. Mini-tablets offer finished dosage form flexibility in that they can be delivered within capsules or sachets.

Such mini-tablets may be presented in a capsule. Capsules may be hard-shelled capsules, which are typically made using gelatin or HPMC (most suitably HPMC) and contain dry, powdered ingredients or miniature pellets made by e.g. processes of extrusion or spheronisation. These are made in two halves: a lower-diameter "body" that is filled and then sealed using a higher-diameter "cap". Alternatively capsules may be soft-shelled capsules. Both of these classes of capsules are made from aqueous solutions of gelling agents, such as animal protein (mainly gelatin) or plant polysaccharides or their derivatives (such as carrageenans and modified forms of starch and cellulose).

The pharmaceutical composition of the invention comprises a compressed core and a pH-sensitive enteric coating, wherein the compressed core comprises a pharmaceutically active binding polypeptide.

"Compressed" as used herein refers to a substance which has undergone compression, i.e. squeezing or pressing.

Suitably the compressed core essentially consists of, or consists of one or more compression aids; one or more disintegrants; one or more lubricants a pharmaceutically active binding polypeptide.

Suitably the hardness of the compressed core is 20-110 N, more suitably 40-100 N, most suitably 60-90 N.

Suitably the compressed core comprises, essentially consists of, or consists of the following: 20-55% one or more compression aids (e.g. mannitol and microcrystalline cellulose); 2-6% one or more disintegrants (e.g. croscarmellose sodium); 0.1-2% one or more lubricants (e.g. magnesium stearate) and 40-80% pharmaceutically active binding polypeptide (e.g. an immunoglobulin chain variable domain); all by weight relative to the weight of the core. More suitably the compressed core comprises, essentially consists of, or consists of the following: 30-40% one or more compression aids (e.g. mannitol and microcrystalline cellulose); 3-5% one or more disintegrants (e.g. croscarmellose sodium); 0.5-1.5% one or more lubricants (e.g. magnesium stearate) and 50-70% pharmaceutically active binding polypeptide (e.g. an immunoglobulin chain variable domain); all by weight relative to the weight of the core.

Suitably, the pharmaceutically active binding polypeptide is present at 30-80%, such as 40-75%, such as about 50%-60% by weight relative to the weight of the core.

Therapeutic Use and Delivery

The pharmaceutical composition of the invention is suitably for administration to a human. A therapeutically effective amount of a pharmaceutical composition of the invention is an amount which is effective, upon single or multiple dose administration to a subject, in treating or preventing disease in a subject. A therapeutically effective amount may vary according to factors such as the disease state, age, sex, and weight of the individual, and the ability of the pharmaceutical composition to elicit a desired response in the individual. A therapeutically effective amount is also one in which any toxic or detrimental effects of the pharmaceutical composition are outweighed by the therapeutically beneficial effects.

A pharmaceutical composition of the invention is formulated for oral delivery. A key problem with oral delivery is ensuring that sufficient pharmaceutically active binding polypeptide reaches the area of the intestinal tract where it is required. Factors which prevent a polypeptide reaching the area of the intestinal tract where it is required include the presence of proteases in digestive secretions which may degrade the polypeptide. Suitably, the polypeptide is substantially stable in the presence of one or more of such proteases by virtue of the inherent properties of the polypeptide itself. Suitably, the polypeptide is substantially stable when exposed to a region of the intestinal tract. Alternatively, a large dose of polypeptide may be administered to compensate for quantities of polypeptide becoming degraded in the intestinal tract.

It is known that proteins delivered directly to the ileum can be immunogenic whereas the same proteins delivered orally and subjected to stomach and duodenal digestion, induce immunological tolerance (see Michael 1989). The compositions of the invention are enterically coated resulting in, on oral administration, pharmaceutically active binding polypeptide being first exposed to the subject's immune system when released in a region of the intestinal tract such as in the ileum. The skilled person may view such a delivery method as immunologically equivalent to direct delivery to the ileum. It is surprising and highly advantageous therefore that an immunologically tolerant response has been observed in respect of the orally-administered compositions of the invention.

A surfactant may also be added to the pharmaceutical composition to reduce aggregation of the polypeptide and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

The pharmaceutically active binding polypeptide may be lyophilised. A lyoprotectant may be added in order to protect the polypeptide against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

Alternatively, the pharmaceutically active binding polypeptide may be spray dried.

The dosage ranges for administration of the pharmaceutical composition of the invention are those to produce the desired therapeutic effect. The dosage range required depends on the precise nature of the pharmaceutical composition, the age of the patient, the nature, extent or severity of the patient's condition, contraindications, if any, and the judgement of the attending physician. Variations in these dosage levels can be adjusted using standard empirical routines for optimisation.

Suitable human dosages of the pharmaceutically active binding polypeptide are in the range of 10 mg-5000 mg, such as 50 mg-1500 mg, such as 100 mg-500 mg. Suitable dosages of the pharmaceutically active binding polypeptide per kg of body weight are in the range of 1 mg-500 mg, such as 5 mg-150 mg, such as 10 mg-50 mg. The human dose or the dose per kg bodyweight may be administered daily or more frequently, for example 2, 3 or 4 times per day or less frequently for example every other day or once per week, once per fortnight or once per month. More suitably the dose is administered 3 times per day.

In one aspect of the invention there is provided the use of the pharmaceutical composition in the manufacture of a medicament for the treatment of autoimmune and/or inflammatory diseases of the intestinal tract. In a further aspect of the invention there is provided a method of treating autoimmune and/or inflammatory diseases of the intestinal tract comprising administering to a person in need thereof a therapeutically effective amount of the pharmaceutical composition.

The word 'treatment' is intended to embrace prophylaxis as well as therapeutic treatment. Treatment of diseases also embraces treatment of exacerbations thereof and also embraces treatment of patients in remission from disease symptoms to prevent relapse of disease symptoms.

Diseases of the Intestinal Tract

Suitably the pharmaceutical composition of the invention is for use in the treatment or prevention of diseases of the intestinal tract. Diseases of the intestinal tract relate to diseases affecting the small intestine and large intestine. The small and large intestines may be affected by infectious, autoimmune and other types of diseases.

Autoimmune Diseases and/or Inflammatory Diseases of the Intestinal Tract (IT)

The chronic inflammatory bowel diseases (IBD) Crohn's disease and ulcerative colitis, which afflict both children and adults, are examples of autoimmune and inflammatory diseases of the IT (Hendrickson et al., 2002, herein incorporated by reference in its entirety). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al., 2002, herein incorporated by reference in its entirety). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of gastrointestinal symptoms. Patients who have ileocolonic involvement usually have postprandial abdominal pain, with tenderness in the right lower quadrant and an occasional inflammatory mass. Symptoms associated with gastroduodenal Crohn's disease include early satiety, nausea, emesis, epigastric pain, or dysphagia. Perianal disease is common, along with anal tags, deep anal fissures, and fistulae (Hendrickson et al., 2002, herein incorporated by reference in its entirety).

Suitably the polypeptide, pharmaceutical composition or construct of the invention is for use in the treatment of an autoimmune and/or inflammatory disease of the IT selected from the list consisting of Crohn's disease, ulcerative colitis, irritable bowel disease, diabetes type II, glomerulonephritis, autoimmune hepatitis, Sjogren's syndrome, celiac disease and drug- or radiation-induced mucositis; more suitably Crohn's disease, ulcerative colitis, irritable bowel disease, celiac disease and drug- or radiation-induced mucositis; more suitably Crohn's disease, ulcerative colitis and irritable bowel disease; most suitably Crohn's disease.

Combination Therapy

It is within the scope of the invention to use the pharmaceutical composition of the invention in therapeutic methods for the treatment of autoimmune diseases as an adjunct to, or in conjunction with, other established therapies normally used in the treatment of autoimmune diseases.

For the treatment of IBD (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-IL-6R antibodies (e.g. tocilizumab), anti-IL-6 antibodies, anti-TNF-alpha antibodies (e.g., infliximab, adalimumab, certolizumab pegol or golimumab); anti-IL12/IL23 antibodies (e.g., ustekinumab); anti-IL6R antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are tocilizumab, infliximab, adalimumab, certolizumab pegol or golimumab.

Hence another aspect of the invention provides a pharmaceutical composition of the invention in combination with one or more further active agents, for example one or more active agents described above.

In a further aspect of the invention, the pharmaceutical composition is administered sequentially, simultaneously or separately with at least one active agent selected from the list above.

Similarly, another aspect of the invention provides a combination product comprising:

(A) a pharmaceutical composition of the present invention; and (B) one or more other active agents, wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a pharmaceutical composition of the present invention and another therapeutic agent, in admixture with a pharmaceutically acceptable adjuvant, diluent or carrier.

The invention also encompasses a kit-of-parts comprising components:

(i) a pharmaceutical composition of the present invention in admixture with a pharmaceutically acceptable adjuvant, diluent or carrier; and (ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of autoimmune diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Suitably the pharmaceutical composition of the invention is for use as a medicament and more suitably for use in the treatment of an autoimmune and/or inflammatory disease.

Preparative Methods

Dry granulation followed by compression or alternatively direct compression may be used to manufacture the compressed core. Powders that can be mixed well do not require granulation and can be compressed into tablets through direct compression. These methods are particularly appropriate if the composition of the invention is to be delivered as a tablet, such as a mini-tablet.

Granulation processes create granules by light compaction of the powder blend under low pressures. The compacts so-formed are broken up gently to produce granules (agglomerates). This process is often used when the product to be granulated is sensitive to moisture and heat. Dry granulation can be conducted on a tablet press using slugging tooling or on a roll press called a roller compactor. Pressures may be varied to attain proper densification and granule formation.

Components may be added to the pharmaceutical composition during manufacture such that the components become extragranular or intragranular. If the component is mixed with other components prior to granulation, which is further prior to tablet compression to form the core, the component will be incorporated into the granules and will thus be intragranular. If the component is mixed with formed dry granules before tablet compression to form the core, the component will be extragranular.

Compressed cores may be fabricated by direct compression by punches and dies fitted to a tabletting press, ejection or compression molding, granulation followed by compression, or forming a paste and extruding the paste into a mold or cutting the extrudate into short lengths and optionally using a spheroniser to round the edges of the lengths so formed. Suitably, the process used for preparing compressed cores is dry granulation of the component mixture followed by compression, preferably into mini-tablets. Suitably compression is carried out using a tabletting press such as a single punch machine (e.g. a Manesty F3) or a rotary tablet press (e.g. a Manesty Technipress, suitably using a top cam compression force setting of 29).

In producing the pharmaceutical composition of the invention, suitably the pharmaceutically active binding polypeptide is dry granulated to form granules. More suitably the pharmaceutically active binding polypeptide (e.g. an immunoglobulin chain variable domain) and one or more compression aids (e.g. mannitol) are granulated together. More suitably the pharmaceutically active binding polypeptide (e.g. an immunoglobulin chain variable domain), one or more compression aids (e.g. mannitol) and one or more lubricants (e.g. magnesium stearate) are granulated together. These components therefore become intra-granular. The granules so produced may then suitably be compressed to form the compressed core.

Alternatively, after granulation, suitably the one or more compression aids (e.g. microcrystalline cellulose), the one or more disintegrants (e.g. croscarmellose sodium) and the one or more lubricants (e.g. magnesium stearate) are blended with the granules, followed by compression to form the compressed core.

As used herein, 'intra-granular' means present within granules (before compression) and 'extra-granular' means present between granules (after compression).

In one aspect of the invention there is provided a method of producing the pharmaceutical composition of the invention wherein (i) a pharmaceutically active binding polypeptide, one or more compression aids and one or more lubricants are dry granulated together to form granules, wherein the pharmaceutically active binding polypeptide is an immunoglobulin chain variable domain, the one or more compression aids is mannitol and the one or more lubricants is magnesium stearate, followed by (ii) blending with the granules one or more compression aids, one or more disintegrants and one or more lubricants, wherein the one or more compression aids is microcrystalline cellulose, the one or more disintegrants is croscarmellose sodium and the one or more lubricants is magnesium stearate, followed by (iii) compressing the blend to form a compressed core; wherein the compressed core consists of 20-55% mannitol and microcrystalline cellulose; 2-6% croscarmellose sodium; 0.1-2% magnesium stearate and 40-75% immunoglobulin chain variable domain all by weight relative to the weight of the core, followed by (iv) coating the compressed core with a pH sensitive enteric coating. In a further aspect the invention provides a pharmaceutical composition obtainable by the preceding method.

pH sensitive enteric coatings may be applied using organic solvent, using aqueous solution or using a mixture of organic solvent and water. Greater quantities of pH sensitive enteric polymer coat should be included when using an entirely aqueous solution coating process.

According to one aspect of the invention there is provided a method of making the pharmaceutical composition according to the invention comprising compressing a blend of the pharmaceutically active binding polypeptide and the one or more excipients to form a core, followed by coating the core with a pH sensitive enteric coating. Suitably the core is coated in a sub-coat before coating with a pH sensitive enteric coating.

The present invention will now be further described by means of the following non-limiting examples.

EXAMPLES

Example 1: Formulation

A solid pharmaceutical composition according to the invention was produced in the form of mini-tablets by dry granulation and compression. The mini-tablets were then presented in different presentations, wherein each presentation contained a different quantity of mini tablets in different sizes of capsules. The main presentation used in the examples detailed below was a size 00 HPMC capsule containing 15 enterically coated mini-tablets (total 185 mg of pharmaceutically active binding polypeptide). The mini-tablet cores had a diameter of 3 mm (excluding coating thickness) and a hardness of approximately 90 N.

The components contained in each mini-tablet and therefore in the 15 mini-tablets contained in the capsule are listed in Table 2 below.

TABLE 2

| Name of mini tablet component | Function | % w/w in composition | Quantity (mg/capsule) 185 mg dose (15 mini-tablets) | Quantity (mg) 12 mg dose (1 mini-tablet) |
|---|---|---|---|---|
| Mini-tablet cores | | | | |
| Total polypeptide | Active pharmaceutical ingredient (API) | 45.7 | 225 | 15 |
| Mannitol | Compression aid | 12.0 | 59.25 | 3.95 |
| Microcrystalline cellulose | Compression aid | 14.6 | 72 | 4.8 |
| Croscarmellose sodium | Super disintegrant | 3.1 | 15 | 1 |
| Magnesium stearate | Lubricant | 0.8 | 3.75 | 0.25 |
| Sub coating | | | | |
| Hydroxypropyl-methyl cellulose pH sensitive enteric coating | Polymer coat | 3.8 | 18.75 | 1.25 |
| Eudragit ® L100 | Enteric polymer coat | 11.7 | 57.76 | 3.85 |

TABLE 2-continued

| Name of mini tablet component | Function | % w/w in composition | Quantity (mg/capsule) 185 mg dose (15 mini-tablets) | Quantity (mg) 12 mg dose (1 mini-tablet) |
| --- | --- | --- | --- | --- |
| Triethyl citrate | Plasticiser | 2.3 | 11.51 | 0.77 |
| Talc | Anti-tacking agent | 5.9 | 28.93 | 1.93 |
| Sodium lauryl sulphate | Surfactant | 0.04 | 0.20 | 0.01 |

The total polypeptide in the composition has a purity of approximately 70-90% such that 225 mg of polypeptide contains 185 mg of pharmaceutically active binding polypeptide.

The pharmaceutically active binding polypeptide used throughout the examples is one of the ICVDs recited in SEQ ID Nos: 1-28. This is a 115 amino acid, 12.6 kDa polypeptide. The pI of the polypeptide is 6.8 and the polypeptide has an aqueous solubility of greater than 30 mg/mL. The ICVD binds with high affinity to, and has potent neutralising activity against, human and Cynomolgus monkey TNF-alpha.

The mini-tablets were produced by the following methodology.

The lyophilised polypeptide was blended with mannitol and a portion of the magnesium stearate and dry slugged to increase its density. This material was then passed through a screen, blended with the other mini-tablet excipients (microcrystalline cellulose, croscarmellose sodium and the remaining magnesium stearate) and compressed to produce the mini-tablets. The mini-tablets were then coated with a 5% solution of hydroxylpropyl methyl cellulose in ethanol:water 80:20, dried and the solvent removed to create a sub-coat and a smoother surface. The mini-tablets were then coated with Eudragit® L100 polymer, together with triethyl citrate, talc and sodium lauryl sulphate, as an organic solution in isopropyl alcohol and water and dried to create a pH-sensitive enteric coat, such that each mini-tablet gained 25% weight. The resulting approximately 3 mm diameter mini-tablets were then filled into capsules the doses given above.

Two separate batches of mini-tablets were produced on different occasions. These batches are referred to herein as Batch A and Batch B. Both batches contain identical quantities of components as listed in Table 1. The pH sensitive enteric coating on Batch A had a thickness of 100-170 um while the pH sensitive enteric coating on Batch B had a thickness of 70-170 um.

Example 2: The Pharmacopeial Enteric Coating Test

Prior studies (not shown) established that the sub-coated compressed core needed to gain greater than 17% additional weight on addition of pH sensitive enteric coating optimal release timing.

Six capsules of Example 1 containing mini-tablets from Batch A were subjected to the Pharmacopeial Enteric Coating Test, one capsule per vessel.

Reference standards were prepared containing 0.0206 mg/mL and 0.206 mg/mL of ICVD.

The capsules promptly dissolved as expected, releasing the mini-tablets to the acid environment.

It was found that the mini-tablets released less than 10% of the ICVD during the two hour period of the test (data not shown). The composition is therefore compliant with the dissolution requirements for delayed-release solid dosage forms administered orally set out in European Pharmacopoeia 8.0, 2.9.3, "Dissolution test for solid dosage forms".

During repeat testing, when the composition was left in the testing medium with continued stirring for greater than 2 hours, it was established by visual inspection (and by there being no increase in UV280 nm) that the enteric coat maintained integrity for greater than or equal to 6 hours.

Example 3: The Pharmacopeial Dissolution Test

After testing the mini-tablets from each of the six vessels in the Pharmacopeial Enteric Coating Test as detailed in Example 2, the mini-tablets from each of the six vessels were then tested using the Pharmacopeial Dissolution Test, as detailed above. The results of the test are shown in Table 3, FIG. 1 (data points for individual vessels 1-6) and FIG. 2 (average for vessels 1-6, with the dissolution ranges which are recited under "Measurement of sustained release: The Pharmacopeial Dissolution Test" above, illustrated by arrows).

TABLE 3

| Time (minutes) | % Dissolution |
| --- | --- |
| 5 | 0.6 |
| 10 | 1.5 |
| 15 | 2.3 |
| 30 | 16.6 |
| 45 | 29.0 |
| 60 | 41.6 |
| 90 | 63.1 |
| 120 | 71.3 |
| 150 | 73.5 |

In summary, it can be seen that sustained release of pharmaceutically active binding polypeptide was achieved. Sustained release was achieved over the course of approximately 2 to 2.5 hours. This release profile was expected to translate to an ideal sustained release profile in vivo. This expectation was confirmed by the in vivo experiments detailed below.

Example 4: The Dynamic Dissolution Test

The solid pharmaceutical composition detailed above under Example 1 was tested using the Dynamic Dissolution Test. Six samples, each sample containing 15 mini-tablets from Batch A and six samples, each sample containing 11 mini-tablets from Batch B, were tested. The conditions used for each sample of 15 Batch A mini-tablets were in line with The Dynamic Dissolution Test detailed above. The conditions used for each sample of 11 Batch B mini-tablets varied from The Dynamic Dissolution Test in that 800 mL of 0.1M HCl was used per sample.

Figure 4:
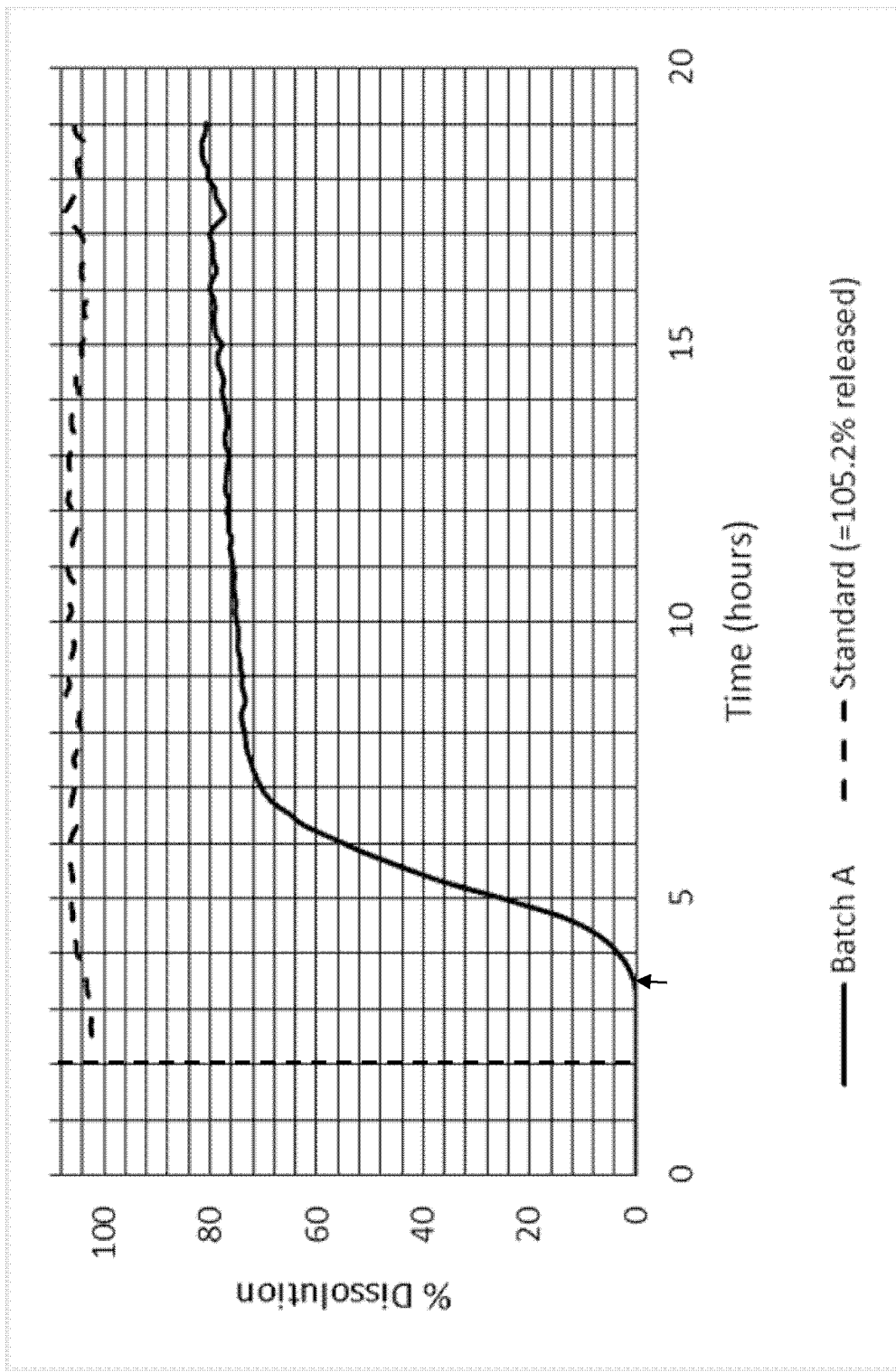
Figure 5:
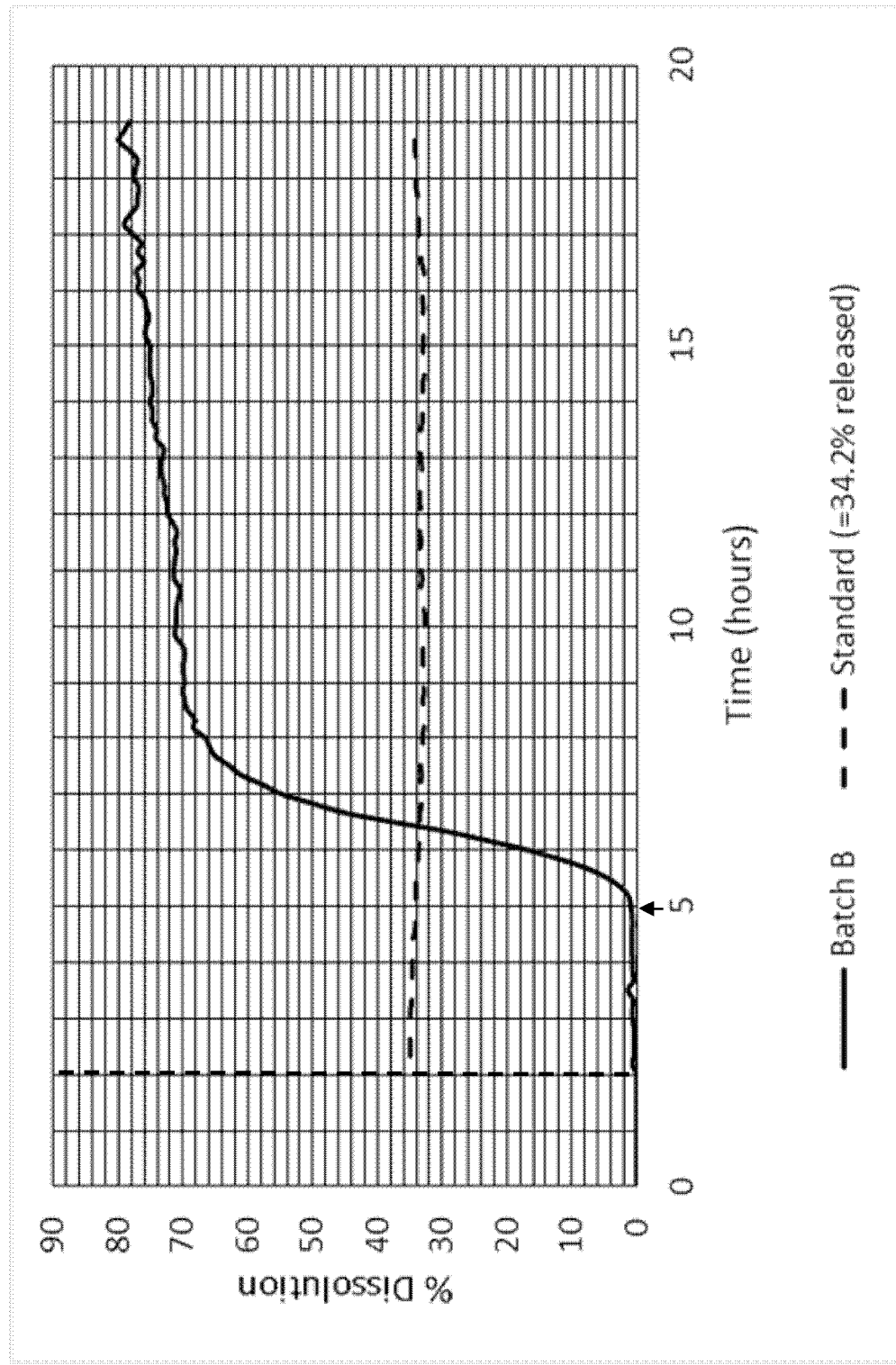
FIG. 5—% dissolution of pharmaceutically active binding polypeptide in The Dynamic Dissolution Test (Batch B)

No dissolution of ICVD from the mini-tablets took place during the acid stage for any sample of either Batch A (FIG. 4, curve preceding 2 hour point) or Batch B (FIG. 5, curve preceding 2 hour point).

These same mini-tablets were then transferred to Hanks buffer according to The Dynamic Dissolution Test. Transfer to Hanks buffer (2 hour point) is denoted by an upright dotted line in FIGS. 3, 4 and 5.

A stock and working solution was prepared. The stock solution was prepared in the dissolution vessel filed with 798.5 mL of pre conditioned Hanks hydrogen carbonate buffer solution of pH 5.79 by adding of 1.50 mL ICVD standard solution (known quantity and concentration of ICVD). The samples of dissolution media were filtrated during sampling over a 1 µm Poroplast-filter (PES, Dissolution Accessories, Amsterdam, Netherlands) and measured without further pre-treating. Amount of the dissolved drug was determined by means of UV-Vis spectroscopy (Agilent 8453, Agilent Technologies, Santa Clara, USA) in close loop mode. The absorbance was measured using quartz flow through cells (Hellma, Müllheim, Germany) with 10 mm light path in differential mode at 279 (signal) and 450-550 nm (background subtraction over range).

The amount of the dissolved ICVD was calculated individually based on the mean standard absorbance according to the equation given below:

$$\text{ICVD dissolved} = A*V*F$$

Wherein:
A—Measured absorbance of the sample
V—Corrected volume
F—Calibration factor obtained based on the absorbance of the standard solution The volume correction of the sample and standard solution were performed individually. The volume of the dissolution medium of the standard and test solutions was measured at the end of the test. It was assumed that the volume contraction due to the evaporation was linear over time and the volume of the sample and standard solutions were calculated for each sampling point individually and were accordingly considered in the calculations.

When testing the Batch A mini-tablet samples, it was found that greater than 1% of the polypeptide first started to be released after 1.67 hours from first transfer to Hanks buffer (see FIG. 4, region after transfer to Hanks buffer at 2 hours). When testing Batch B, it was found that greater than 1% of the polypeptide first started to be released after 3.17 hours from first transfer to Hanks buffer (see FIG. 5, region after transfer to Hanks buffer at 2 hours).

This time point, at which greater than 1% of the pharmaceutically active binding polypeptide has first started to be released, is the 'start of release'. The start of release is denoted by an arrow in FIGS. 4 and 5. These time periods for both batches are suitable for a delayed release product.

The % dissolution of ICVD following start of release was then recorded. The results for Batch A are shown in FIG. 4 (region following start of release at 1.67 hours following first transfer to Hanks buffer at 2 hours) and the results for Batch B are shown in FIG. 5 (region following start of release at 3.17 hours following first transfer to Hanks buffer at 2 hours).

A summary of the % dissolution of ICVD at time points 60, 120 and 180 minutes after start of release is given in Table 4 below.

TABLE 4

| % of ICVD released after start of release | Mean results for Batch A | Mean results for Batch B |
| --- | --- | --- |
| % released 60 mins after start of release | 14.3 | 23.1 |
| % released 120 mins after start of release | 47.1 | 57.7 |
| % released 180 mins after start of release | 67.6 | 68.4 |

After exiting the stomach, transit through the duodenum and jejunum takes approximately 2 hours (see above under "Intestinal Transit Times"). Accordingly, it was expected that the in vitro release profiles above would translate to sustained release profiles in vivo wherein release starts to take place around the distal jejunum, with substantially complete release achieved in the colon. All released ICVD would then be expected to travel through the remaining lower regions of the intestinal tract. This expectation was confirmed by the in vivo examples below.

Example 5: Excipient Compatibility

The effect of the excipients used in the composition on the melting temperature (Tm) of the ICVD was investigated.

Thermal shift assays (TSA) are a common method used in protein biochemistry to examine the effect of solutes on a protein's structure. Certain solutes (salts, excipients etc) may interact with the protein and cause either stabilisation or destabilisation of the protein. This effect can be assessed by comparing the melting temperature (Tm) of the protein with or without the compound in question. Increases in Tm indicate stabilisation, i.e., a strengthening of forces that hold the protein in shape. Decreases in Tm indicate the reverse.

In this assay, the protein is mixed with the hydrophobic dye sypro orange and heated gradually from 25° C. to 98° C. As the proteins melt (unfold, a.k.a. denature), their hydrophobic cores are exposed and sypro orange binds to these residues via hydrophobic interactions. Sypro orange fluoresces only when bound to the protein and, in this manner, the unfolding of the protein is measured in real time by lasers in the qPCR machine. The data from the machine is processed in Graphpad Prism, using Boltzmann curve fitting. The Tm is taken from the inflection point of the Boltzmann curve. Excipients from were mixed in 1×PBS, pH 7.4, or water by vortexing. Any insoluble material was removed by centrifugation and the supernatants taken for assay.

Figure 6:
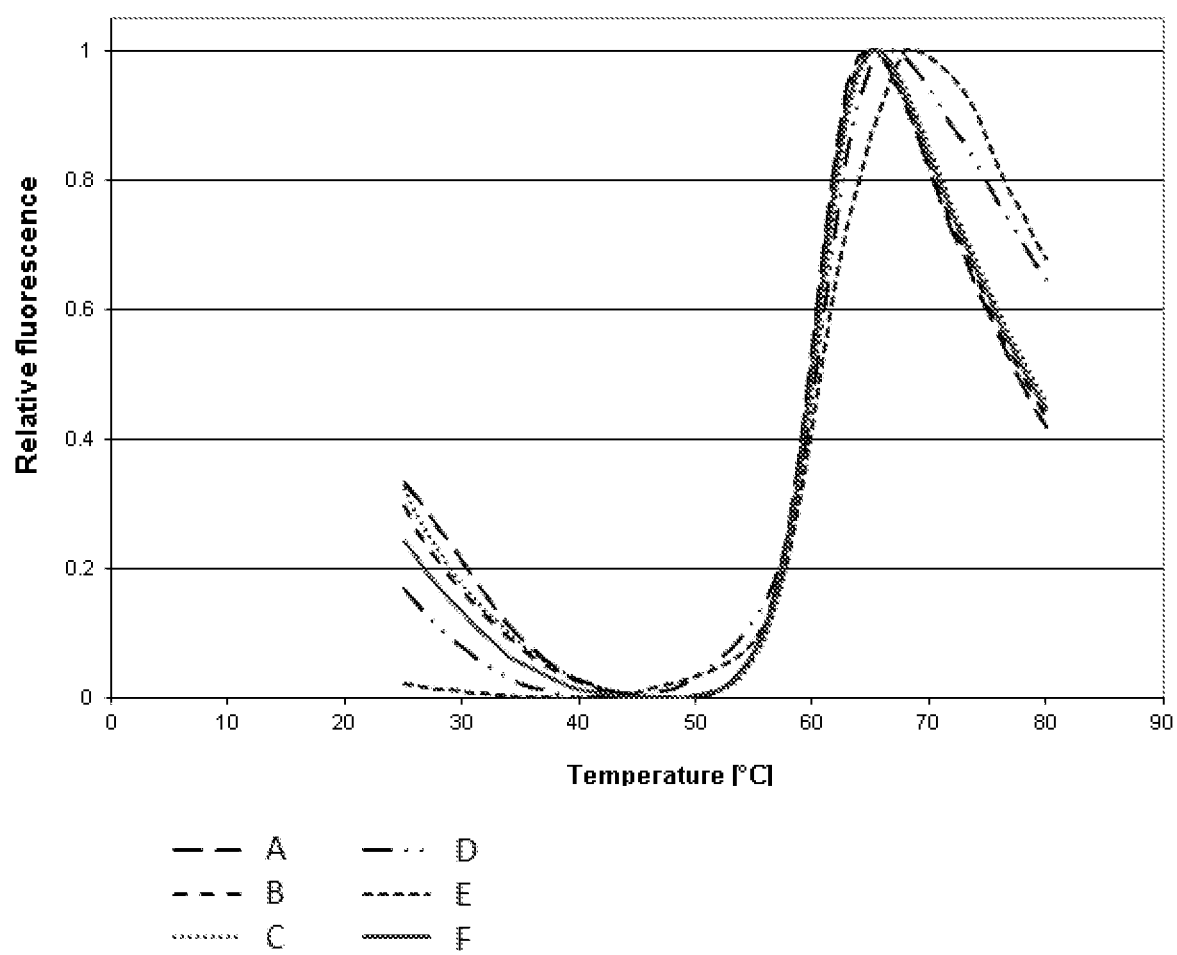
FIG. 6—Thermal shift assay demonstrating the impact of excipients on Tm of pharmaceutically active binding polypeptide FIG. 7—Calculated luminal [anti-TNF ICVD] in cynomolgus monkey gastrointestinal tract sections FIG. 8—Total % recovery of anti-TNF ICVD from cynomolgus monkey gastrointestinal tracts FIG. 9—Humira competition ELISA OD450 data FIG. 10—anti-TNF ICVD concentration in pooled cynomolgus monkey faeces FIG. 11—Calculated anti-TNF ICVD recovered from pooled cynomolgus monkey faeces FIG. 12—Dynamic Dissolution Test comparing spray dried and lyophilised starting materials

The following excipients were tested (labels refer to the legend in FIG. 6).

A—(-0.1° C.) 8.88 uM ICVD; control in 1 (1×PBS pH 7.4)
B—(0.1° C.) 8.88 uM ICVD; 17 mg/ml Avicel PH102 in 1 (1×PBS pH 7.4)
C—(0.5° C.) 8.88 uM ICVD; 17 mg/ml Mannitol in 1 (1×PBS pH 7.4)
D—(0.6° C.) 8.88 uM ICVD; 8 mg/ml AcDiSol in 1 (1×PBS pH 7.4)
E—(1.2° C.) 8.88 uM ICVD; 2 mg/ml magnesium stearate in 1 (1×PBS pH 7.4)
F—(0.2° C.) 8.88 uM ICVD; 17 mg/ml Avicel PH112 in 1 (1×PBS pH 7.4)

Avicel PH102 and Avicel PH112 are types of microcrystalline cellulose and AcDiSol is a type of croscarmellose sodium.

The results are shown in FIG. 6. In summary, it was found that these excipients had no impact (detrimental or otherwise) on the Tm of the protein, as most Tm curves produced with excipient exposure remained substantially the same as control (control is shown as Tm curve 'A'). Surprisingly, it was noted that small improvements in thermal stability of the protein were achieved on exposure to mannitol (+0.5° C.), AciDiSol (+0.6° C.) and magnesium sterate (+1.2° C.).

Example 6: Administration to Cynomolgus Monkeys: Polypeptide Concentration in Different Intestinal Tract Compartments and in Faeces 6.1 Polypeptide Concentration in Different Intestinal Tract Compartments A study was conducted to assess the release profile of a composition similar to that of Example 1 Batch A through regions of the intestinal tract when orally administered to Cynomolgus monkeys. The release profile was assessed by analysis of polypeptide concentration in the different intestinal tract compartments.

A single capsule containing 11 mini-tablets was administered orally to each of three Cynomolgus monkeys (the monkeys are referred to as M234, M236 and M238). The mini-tablet composition varied from that of Example 1 in that each mini-tablet contained an additional 1 mg of methylene blue (dye) and a dose of 141 mg of the ICVD. 8 of the mini-tablets also contained 0.7 mg of isoprenaline. The methylene blue dye was for visual analysis of the distribution of dissolved mini-tablets through the gastrointestinal (GI) tract (not discussed herein) and the isoprenaline was for use in a study monitoring heart rate (not discussed herein).

Four hours after oral dosing, the animals were culled. The gastrointestinal tracts were carefully removed, the different GI compartments ligated then cut and the luminal contents and washes collected. The number of undissolved and partially dissolved mini tablets were noted and these mini tablets were removed. The samples were then homogenised and frozen until analysis. After initial centrifugation of the slurries for 5 min at 5000 rpm at 10° C., 1 ml of supernatant was removed from each sample and centrifuged at 13300 rpm in a microfuge at the same temperature for 5 min. The supernatants were then centrifuged again under the same conditions, but for 20 min, after which, they were analysed using a standard Humira competition ELISA (Humira is an anti-TNF-alpha antibody, also known as adalimumab). All dilutions of samples and Humira and the ICVD standard were prepared in PBS containing 1% BSA, 0.6M NaCl, 1% human AB serum, 0.05% Tween 20 and 2× protease inhibitors. ICVD concentrations were interpolated from a standard curve using a 4 parameter, non-linear curve fitting equation in GraphPad Prism. ICVD concentrations in undiluted GI tract samples and 0-4 h faecal supernatants were derived by taking the means of the best interpolated data multiplied by the supernatant dilution factor.

No intact mini-tablets were found in the stomach, duodenum, jejunum or ileum of either M236 or M238. In M234, 4 intact mini-tablets were found in the stomach, 1 in the duodenum and 1 in the jejunum. No partially dissolved mini-tablets were found in any GI tract region of any monkey.

Figure 7:
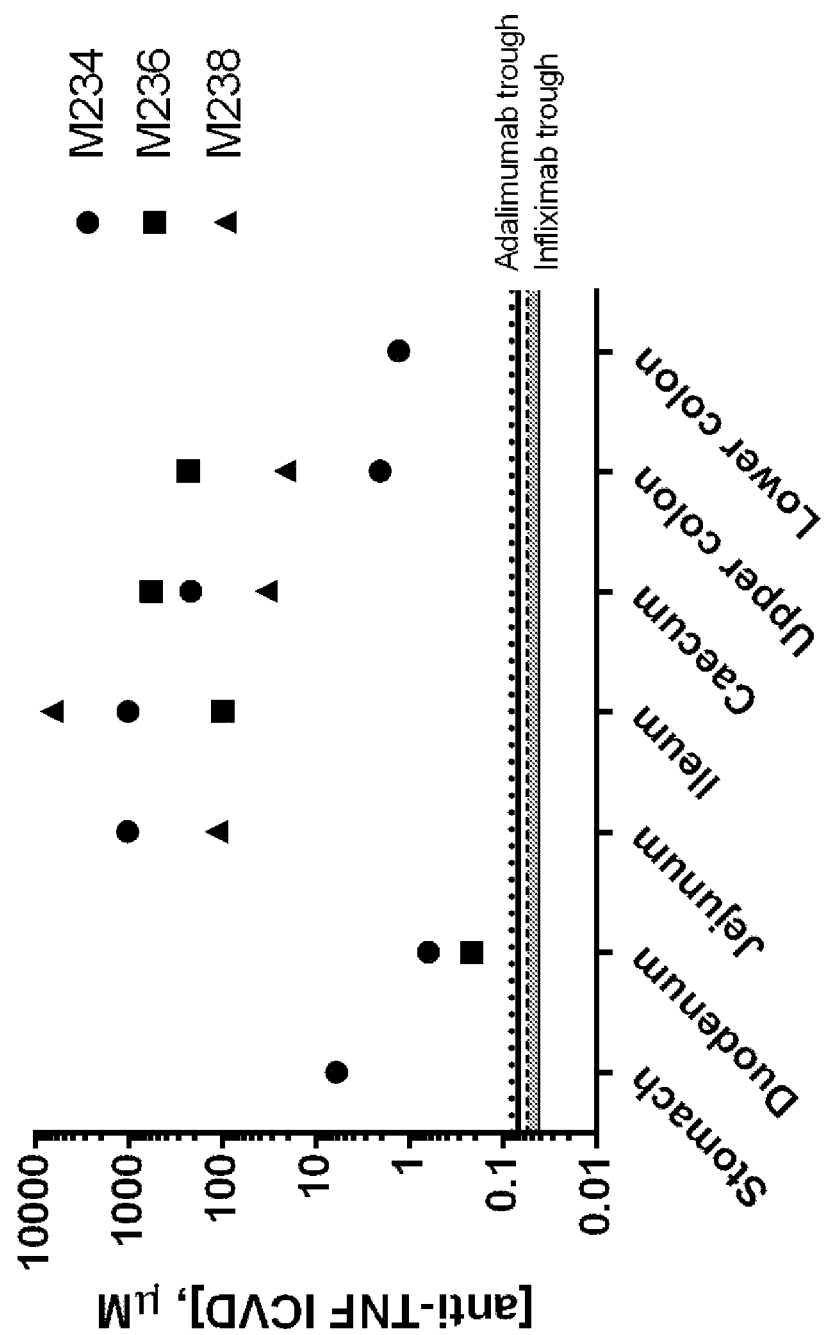

Preparation of the slurry supernatants necessitated adding large volumes of buffer, inevitably diluting the ICVD. In FIG. 7, the expected luminal concentrations of ICVD are presented. These were calculated, assuming that the luminal GI tract contents have a specific gravity of 1, by multiplying the supernatant ICVD concentrations by the fold dilution on addition of buffer. As shown, very high ICVD (0.1→1 mM) are likely to occur in the lumen of some monkey GI tract compartments.

ICVD was only detected in the contents of one Cynomolgus monkey stomach (M234). ICVD was also found at high concentrations in the contents of the ileum, caecum and upper colon of all monkeys. In addition, M234 and M238 were detected at high concentrations in the contents of the jejunum (see FIG. 7)

Figure 8:
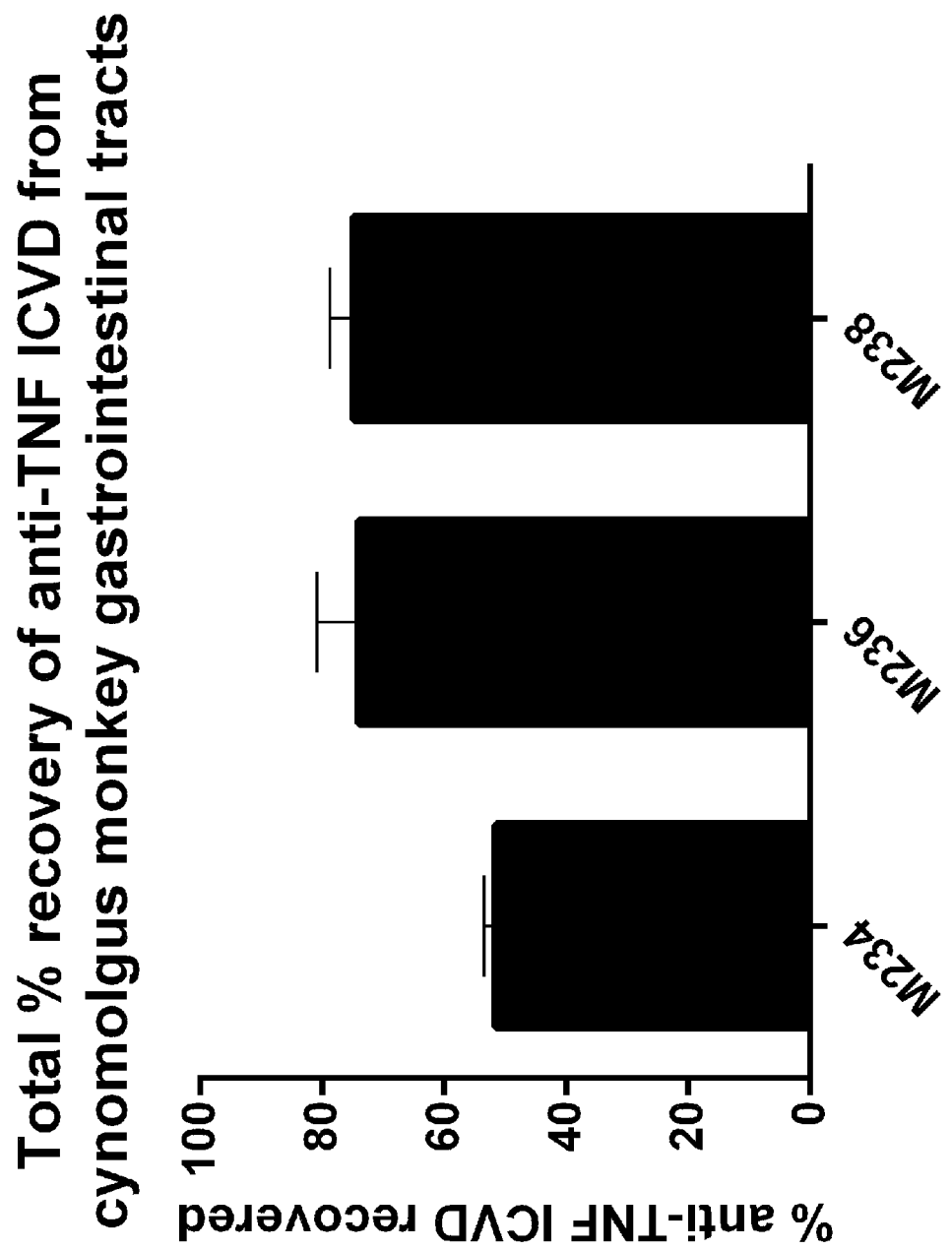

Finally, the % ICVD recovered was calculated, assuming the actual dose at 4 h was delivered by only mini-tablets that had dissolved. As shown in FIG. 8, between 51.5 and 74.9% of the ICVD dose was accounted for.

This study has shown that pharmaceutically active binding polypeptide can be delivered at high concentrations to the lower GI tract of Cynomolgus monkeys. The finding that some mini-tablets remained intact 4 h after dosing suggests that the dose will be delivered over a period of time, offering the potential of prolonged exposure. If these findings are mirrored in treatment of IBD patients when using an anti-TNF-alpha binding polypeptide, then it is reasonable to expect that the concentrations of anti-TNF-alpha polypeptide exposed to the lower GI tract will be more than adequate for effective TNF-alpha neutralisation.

6.2 Polypeptide Concentration in Faeces

A single capsule containing 11 mini-tablets was administered orally to each of three Cynomolgus monkeys. The mini-tablet composition varied from that of Example 1 in that each mini-tablet contained an additional 1 mg of methylene blue (dye) and 8 of the mini-tablets also contained 0.7 mg of isoprenaline. The methylene blue dye was for visual analysis of the dissolution of mini-tablets in faeces and the isoprenaline was for use in a study monitoring heart rate (not discussed herein).

Pooled faeces from the monkeys were collected at 8, 12, 20, 24 and 36 h (no samples were collected at 16 h). No mini-tablets were found in any of the faecal samples. These were mixed with extraction buffer (0.1% BSA, 0.6M NaCl, 0.05% Tween 20, 1× protease inhibitors, 5 mM EDTA in PBS), at 1 g faeces/4 ml buffer, then homogenised and the slurries frozen at −80° C. for storage before analysis. Visual examination revealed blue colouration of the 12 h, 20 h, 24 h and 36 h slurries. Previous in vitro experiments (not shown) have demonstrated that the increasing methylene blue concentration upon dissolution of the mini-tablets is closely correlated with ICVD concentration.

Slurries were thawed and centrifuged for 5 min at 4,000 rpm (3,200 g) to remove the bulk of particulate matter. About 1 ml of each supernatant was transferred to Eppendorf tubes and centrifuged in a microfuge at 13.5K, 10° C. for 5 min, after which supernatants were placed in new tubes and centrifuged for 20 min at 10° C. Supernatants were then used immediately for ICVD measurement using a Humira competition ELISA.

Figure 9:
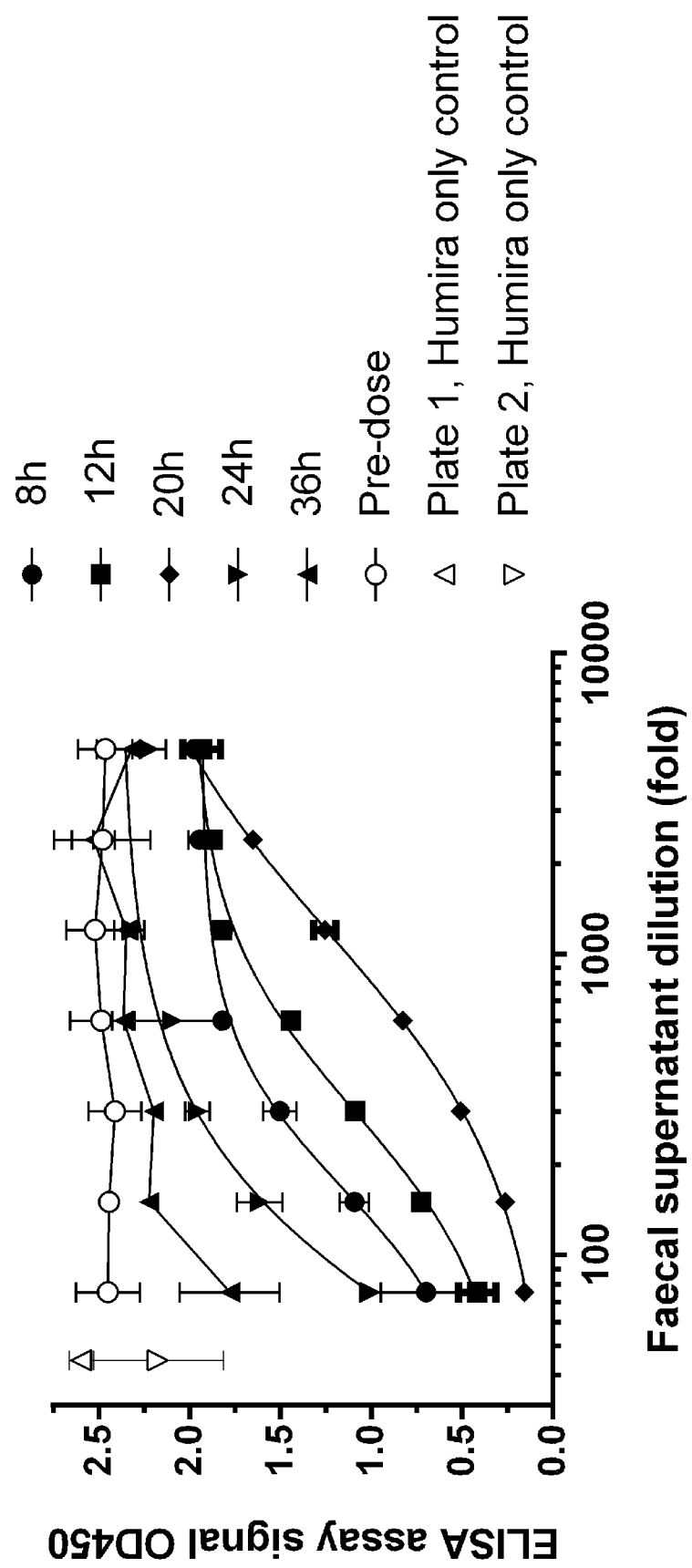

The ELISA OD450 readings for the different faecal supernatants are shown in FIG. 9. The data clearly show that ICVD is present in the faeces supernatant samples at all time points, with the possible exception of the 36 h supernatant (though there may be slight activity visible at the lowest dilution).

Figure 10:
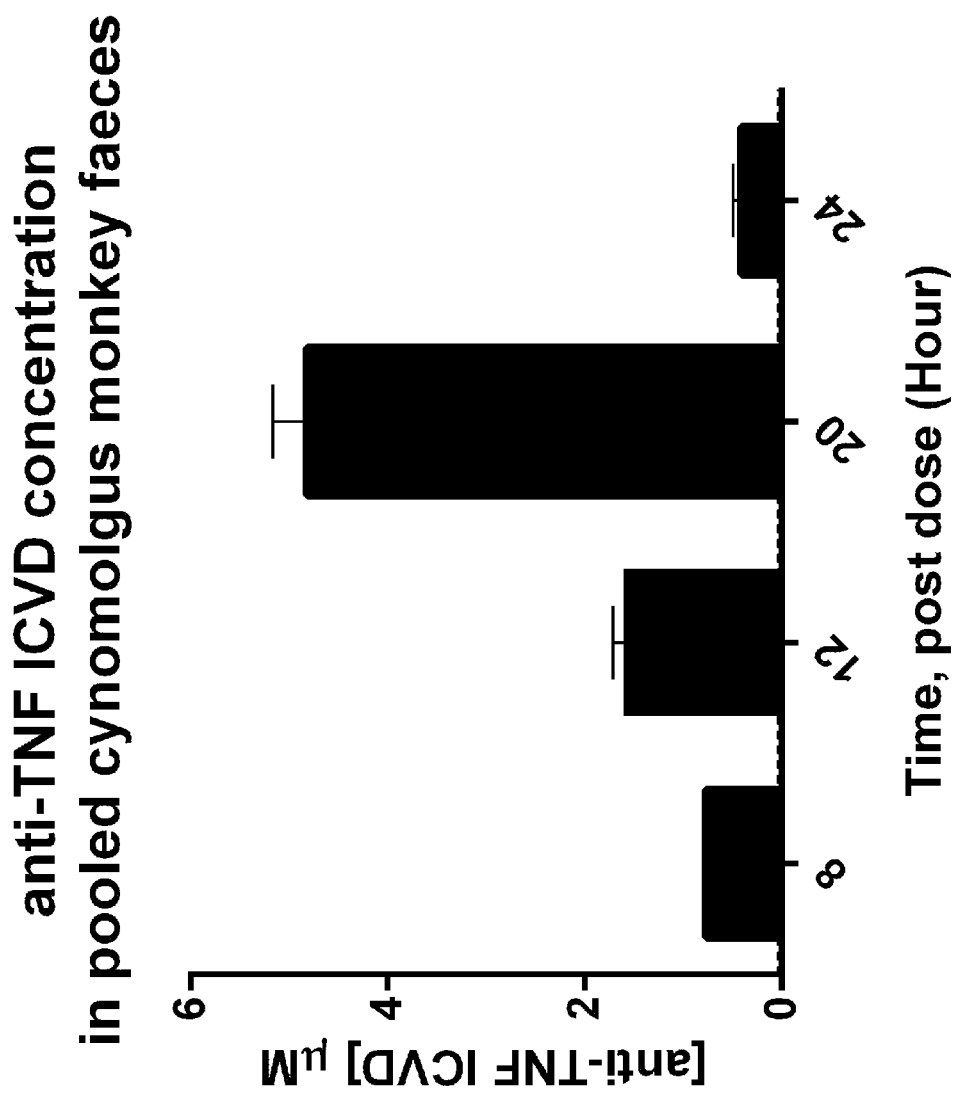

Interpolating these data against standard curves for ICVD using GraphPad Prism and multiplication by the dilution factor of buffer added gave the ICVD concentrations in each faecal sample, using the assumptions that 1 g faeces is equivalent to 1 mL liquid volume and that the polypeptide is uniformly distributed in the faeces. These are shown in FIG. 10.

Figure 11:
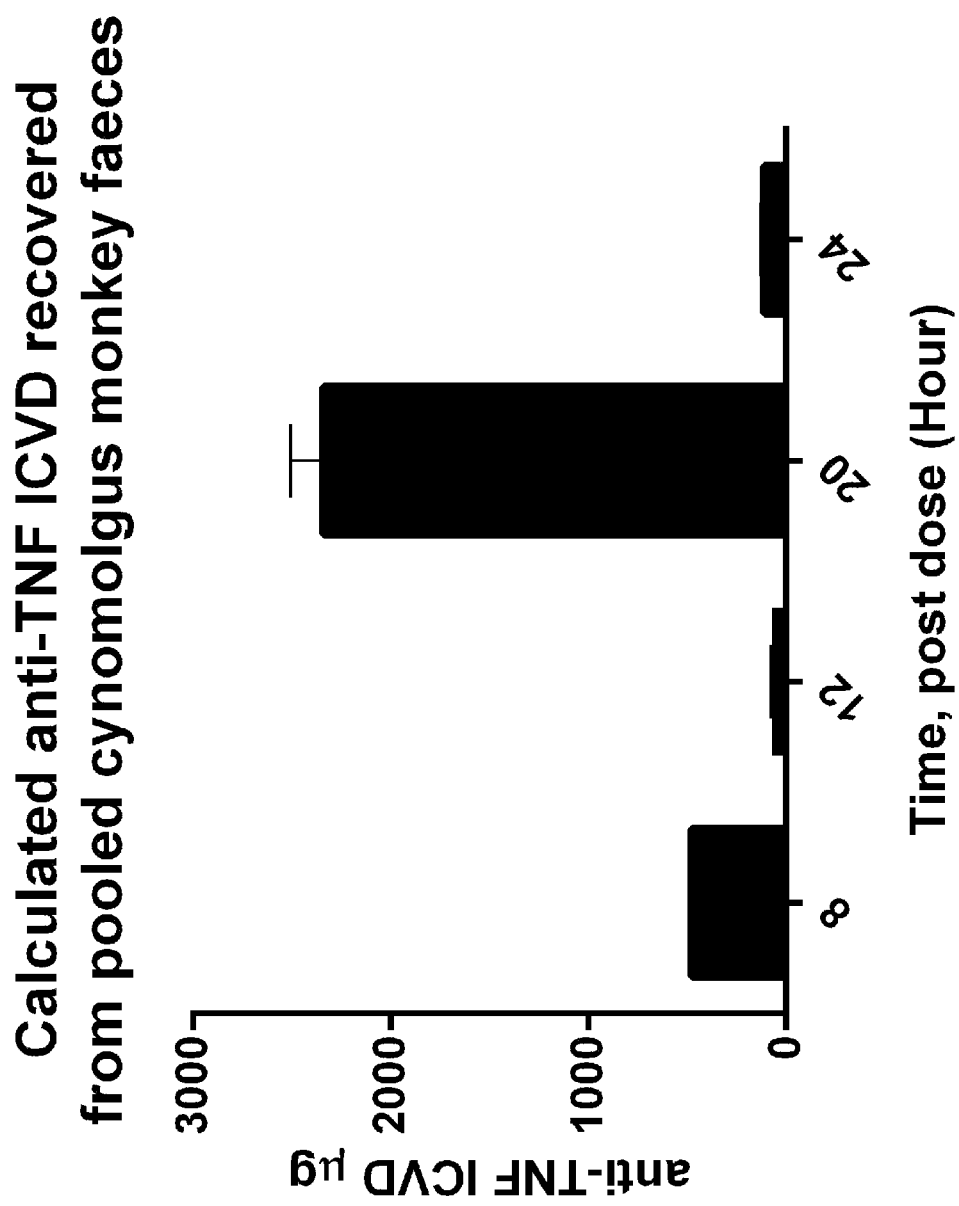

Using slurry volumes (calculated on the basis of 1 g faeces=1 ml, +volume of buffer for extraction) the µg amounts of ICVD in each sample were determined (FIG. 11).

In summary, a sustained substantial concentration of pharmaceutically active binding polypeptide was achieved through the cynomolgus monkey intestinal tract for greater than 8 hours.

Example 7: Administration to Humans: Polypeptide Concentration at the Ileal-Caecal Junction and in Faeces 7.1 Polypeptide Concentration at the Ileal-Caecal Junction The aim of this study was to demonstrate that the pharmaceutically active binding polypeptide incorporated into the composition of Example 1 is delivered at high concentrations to the ileal-caecal junction in man, a major site for Crohn's and the proximal site of Crohn's lesions in the intestine of many patients.

Four human volunteers, fitted with terminal ileostomy bags each received a single oral dose of 1665 mg ICVD, formulated into mini-tabs inside size 00 capsules (9 capsules in total). In these otherwise healthy individuals, the entire contents of the terminal ileum drains into the detachable external bag. At each hourly time point post-dosing, the fitted bag containing the total ileal effluent was removed, frozen and a new bag was fitted. Ileostomy samples were collected in this manner every hour for a period of 12 hours post dosing. Following this time, ileostomy samples were collected every four hours up to 24 hours post dosing. A Pre-dosing sample (day −1) was also taken as a control. Any partially dissolved mini-tablets observed in the bags were removed prior to analysis such that only fully soluble ICVD was analysed. The ICVD was extracted from the ileal fluid and concentrations of active ICVD were determined by functional ELISA, assuming that 1 g ileal fluid is equivalent to 1 mL liquid volume.

The data revealed high concentrations of active ICVD present in the ileostomy bags, in the range 200 nM up to 1 mM. In addition, high concentrations were observed over several hours of bag changes for each subject (see Table 5).

TABLE 5

| Subject | Hour post dose | ICVD concentration in ileal fluid (nM) |
|---|---|---|
| 31001 | 2 | 406350 |
| 31001 | 3 | 305560 |
| 31001 | 4 | 791 |
| 31002 | 2 | 32780 |
| 31002 | 3 | 1130000 |
| 31002 | 4 | 792060 |
| 31002 | 5 | 81750 |
| 31002 | 6 | 12780 |
| 31002 | 7 | 1300 |
| 31002 | 8 | 422 |
| 31002 | 9 | 1410 |
| 31002 | 10 | 7520 |
| 31002 | 11 | 10080 |
| 31002 | 12 | 9210 |
| 31002 | 16 | 6980 |
| 31003 | 3 | 1060000 |
| 31003 | 4 | 496030 |
| 31003 | 5 | 7080 |
| 31003 | 8 | 46110 |
| 31003 | 9 | 75480 |
| 31003 | 10 | 16030 |
| 31003 | 11 | 72940 |
| 31003 | 12 | 15870 |
| 31003 | 16 | 881 |
| 31004 | 2 | 126190 |
| 31004 | 3 | 235 |
| 31004 | 4 | 11110 |
| 31004 | 5 | 3770 |
| 31004 | 6 | 6730 |

ICVD was not detected in any of the predose (Day −1) samples from any subject.

In summary, a sustained and high concentration of pharmaceutically active binding polypeptide was achieved at the ileal-caecal junction in these human volunteers.

7.2 Polypeptide Concentration in Faeces

Healthy male subjects aged 18-45 were dosed orally with a single dose of either 62, 555, 1665 or 4995 mg of ICVD, using the composition detailed in Example 1. Each single dose per subject was administered between 8:30 to 12:00 on day 1. Faecal samples were collected pre dose (either on day −1, or prior to dosing on day 1) and at all available times post dosing up to the morning of day 4 (the end of the study). ICVD was extracted from the faeces and concentrations of active ICVD were determined by functional ELISA, assuming that 1 g faeces is equivalent to 1 mL liquid volume.

High concentrations in the range 180 nM to 724 µM were obtained in the faeces of subjects (see Table 6).

TABLE 6

| Subject ID | mg dose ICVD | Faecal sample collection day | Pre or post dose | [ICVD] in faeces (nM) |
|---|---|---|---|---|
| 11001 | 62 | −1 | PRE DOSE | 0 |
| 11001 | | 1 | POST DOSE | 1013 |
| 13001 | 555 | −1 | PRE DOSE | 0 |
| 13001 | | 2 | POST DOSE | 1052 |
| 13003 | 555 | −1 | PRE DOSE | 0 |
| 13003 | | 1 | POST DOSE | 1938 |
| 13003 | | 2 | POST DOSE | 1511 |
| 14002 | 1665 | −1 | PRE DOSE | 0 |
| 14002 | | 1 | POST DOSE | 5491 |
| 14002 | | 2 | POST DOSE | 558 |
| 14004 | 1665 | −1 | PRE DOSE | 0 |
| 14004 | | 2 | POST DOSE | 27532 |
| 14006 | 1665 | −1 | PRE DOSE | 0 |
| 14006 | | 2 | POST DOSE | 62579 |
| 15001 | 4995 | −1 | PREDOSE | 0 |
| 15001 | | 1 | POST DOSE | 10047 |
| 15001 | | 2 | POST DOSE | 135285 |
| 15001 | | 3 | POST DOSE | 330 |
| 15004 | 4995 | −1 | PREDOSE | 0 |
| 15004 | | 3 | POST DOSE | 273 |
| 15005 | 4995 | 1 | PRE DOSE | 0 |
| 15005 | | 1 | POST DOSE | 724684 |
| 15005 | | 2 | POST DOSE | 258703 |
| 15005 | | 3 | POST DOSE | 3536 |
| 15006 | 4995 | −1 | PRE DOSE | 0 |
| 15006 | | 1 | POST DOSE | 57120 |
| 15006 | | 2 | POST DOSE | 358 |
| 15006 | | 2 | POST DOSE | 186 |

Anti-TNF agents that are used clinically to treat Crohn's disease, such as adalimumab (Humira) and infliximab (Remicade), are administered either by intravenous infusion or subcutaneous injection. Ungar et al. (2016) Clin Gastroenterol Hepatol. 14(4):550-557 state that trough serum levels of 56-83 nM (8-12 µg/mL) for adalimumab and 42-70 nM (6-10 µg/mL) for infliximab are required to achieve mucosal healing in 80%-90% of patients with IBD, and that this could be considered as a "therapeutic window". These trough serum levels are also indicated in FIG. 7 in respect of calculated luminal anti-TNF-alpha ICVD concentrations in cynomolgus monkey gastrointestinal tract sections established above under point 6.1.

Concentrations of anti-TNF-alpha ICVD delivered to the ileal-caecal junction and recovered in the faeces of human volunteers during the clinical work detailed in 7.1 and 7.2 were significantly higher than these levels and are thus predicted to be efficacious as a treatment for Crohn's disease. This assumes that gut luminal concentrations of anti-TNF-alpha ICVD are comparable to serum concentrations of marketed anti-TNF agents with respect to access/penetration to the gut mucosa and sub-mucosa. However, it has been demonstrated in further experimental work (not shown) that this anti-TNF-alpha ICVD of the invention, dosed orally in DSS colitis mice, is able to penetrate to the lamina propia where it is resident for several hours, despite a lack of target (TNF) engagement in mice.

Taken together with the data presented under 7.1 above, these results demonstrate successful delivery of therapeutic levels of ICVD from the ileal-caecal junction to the anus.

Example 8: Administration to Humans: Immunogenicity Study

Protein drugs, including therapeutic antibodies, may elicit an antibody response in patients. Antibodies (of multiple Ig classes) produced in patients that recognise epitopes of protein drugs are termed anti-drug antibodies (ADAs). The presence of ADAs can result in loss of drug efficacy/potency or adverse patient effects (van Schie et al., 2015).

A study was undertaken to assess whether sustained oral dosing in man of the composition of the invention elicits an ADA response. Healthy male subjects aged 18-45 were dosed orally, three times daily, for 14 days with capsules containing 1665 mg (a total of 4995 mg per day) ICVD or placebo, formulated into mini-tabs according to Example 1. Serum samples from subjects were taken prior to dosing, at days 7 and 14 post-dosing, and finally at 28 days (14 days after treatment cessation). These samples were analysed by Sandwich ELISA for the presence of ICVD anti-drug antibodies (ADA). This analysis revealed ADA positive sera, albeit at low titres, from 4 volunteers, two of whom received placebo. In all of these individuals ADAs were present at some level prior to ICVD dosing (pre-existing ADAs).

Analysis of ICVD potency in a TNF-TNFR2 ELISA revealed that ICVD activity against TNF-alpha was unaffected by the presence of all ADA-positive human sera samples at 5%. Therefore, no evidence of ICVD neutralising ADAs was found in the sera of any volunteer at any timepoint (see Table 7).

TABLE 7

| Subject ID | Active or placebo | Sample | ADA sandwich ELISA screening | ADA Titre/serum dilution | ICVD neutralisation |
|---|---|---|---|---|---|
| 21001 | Active | Predose | Negative | | |
| 21001 | Active | Day 7 | Negative | | |
| 21001 | Active | Day 14 | Negative | | |
| 21001 | Active | Day 28 | Negative | | |
| 21002 | Active | Predose | Negative | | |
| 21002 | Active | Day 7 | Negative | | |
| 21002 | Active | Day 14 | Negative | | |
| 21002 | Active | Day 28 | Negative | | |
| 21003 | Active | Predose | Negative | | |
| 21003 | Active | Day 7 | Negative | | |
| 21003 | Active | Day 14 | Negative | | |
| 21003 | Active | Day 28 | Negative | | |
| 21004 | Placebo | Predose | Positive | 64 | No |
| 21004 | Placebo | Day 7 | Positive | 64 | No |
| 21004 | Placebo | Day 14 | Positive | 64 | No |
| 21004 | Placebo | Day 28 | Positive | 64 | No |
| 21005 | Active | Predose | Positive | 64 | No |
| 21005 | Active | Day 7 | Positive | 32 | No |
| 21005 | Active | Day 14 | Positive | 32 | No |
| 21005 | Active | Day 28 | Positive | 32 | No |
| 21006 | Active | Predose | Negative | | |
| 21006 | Active | Day 7 | Negative | | |
| 21006 | Active | Day 14 | Negative | | |
| 21006 | Active | Day 28 | Negative | | |
| 21007 | Active | Predose | Negative | | |
| 21007 | Active | Day 7 | Negative | | |
| 21007 | Active | Day 14 | Negative | | |
| 21007 | Active | Day 28 | Negative | | |
| 21008 | Active | Predose | Positive | 4 | No |
| 21008 | Active | Day 7 | Positive | 4 | No |
| 21008 | Active | Day 14 | Positive | 8 | No |
| 21008 | Active | Day 28 | Positive | 128 | No |
| 21009 | Placebo | Predose | Positive | 8 | No |
| 21009 | Placebo | Day 7 | Positive | 8 | No |
| 21009 | Placebo | Day 14 | Positive | 16 | No |
| 21009 | Placebo | Day 28 | Positive | 8 | No |
| 21010 | Active | Predose | Negative | | |
| 21010 | Active | Day 7 | Negative | | |
| 21010 | Active | Day 14 | Negative | | |
| 21010 | Active | Day 28 | Negative | | |

Example 9: Spray Drying as an Alternative to Lyophilisation

Work was carried out to confirm that the ICVD used in the exemplified composition could be initially prepared by spray drying, instead of lyophilisation, before incorporation into the composition of the invention.

To perform spray drying, a solution containing the ICVD is fed through an atomiser to create a spray, which is exposed to a suitable gas stream to promote rapid evaporation. When sufficient liquid mass has evaporated, the remaining solid material in the droplet forms an individual particle, which is then separated from the gas stream using a filter or a cyclone.

A 3,000 mL sample of ICVD solution was used for the spray-drying process. This consisted of a solution of approximately 22 mg/mL ICVD in 20 mM sodium acetate (3,000 mL of 20 mM sodium acetate (MWt 82.0) equates to 4.92 g of solid. 22 mg/mL ICVD in 3000 mL equates to 66 g. Hence total solids=70.92 g of which 93.1% is ICVD). This small amount of buffer component was not considered to impact the spray drying process or the drug substance characteristics.

Details of the processing conditions used are provided in Table 8 below. 80.4 g of spray-dried material was collected with a water content of 4.4%. Hence this contained 76.86 g of dry material (consisting of approximately 66 g of ICVD, 4.92 g sodium acetate+traces of salts, carbohydrates and host cell proteins).

TABLE 8

| | |
|---|---|
| Batch Size (mL) | 3,000 |
| Nozzle type | 2-fluid |
| Atomisation pressure (psig) | 10 |
| Liquid flow (g/min) | 10 |
| Drying Gas Flow (g/min) | 500 |
| Inlet temperature (° C.) | 145 |
| Outlet temperature (° C.) | 60 |
| Outlet relative humidity (%) | 15.8 |
| Dry Powder Collected (g) | 80.4 |

Nozzle details: Spraying Systems ¼ J Series, 1650/64 Liquid Cap/Air Cap.

Manufacture of mini-tablets from the spray-dried material followed the standard process discussed above in respect of lyophilised material. Due to the small quantity of spray-dried material available and hence the number of mini-tablets produced these had to be bulked out with placebo mini-tablets of a similar size. The placebo mini-tablets were coloured brown to distinguish them from the spray-dried tablets. On coating first with an HPMC base and then with a Eudragit enteric coat the brown colouring of the placebos proved an insufficient contrast and it became difficult to distinguish the placebos from the actives. Consequently, the enteric coating was stopped after approximately an 18% weight gain had been achieved (against a target of 25% weight gain) to ensure these were not 'over-coated'.

15 mini-tablets produced from the spray-dried material were filled into size 00 opaque pink HPMC capsules to give a nominal dose of 185 mg ICVD, along with placebo mini-tablets for bulking.

Tests were performed on these mini-tablets and the findings are detailed in Table 9 below.

TABLE 9

| Test | Result |
|---|---|
| Disintegration (in acid) | Mini-tablets remain complete after 2 hours |
| Disintegration (in phosphate buffer) | Fully disintegrated after 1 hour |
| Content by RP-HPLC | 99% |
| Purity by RP-HPLC | 92% |
| ICVD quantitation by ELISA | 125.1% |
| ICVD purity by SDS-PAGE | 100% |

Figure 12:
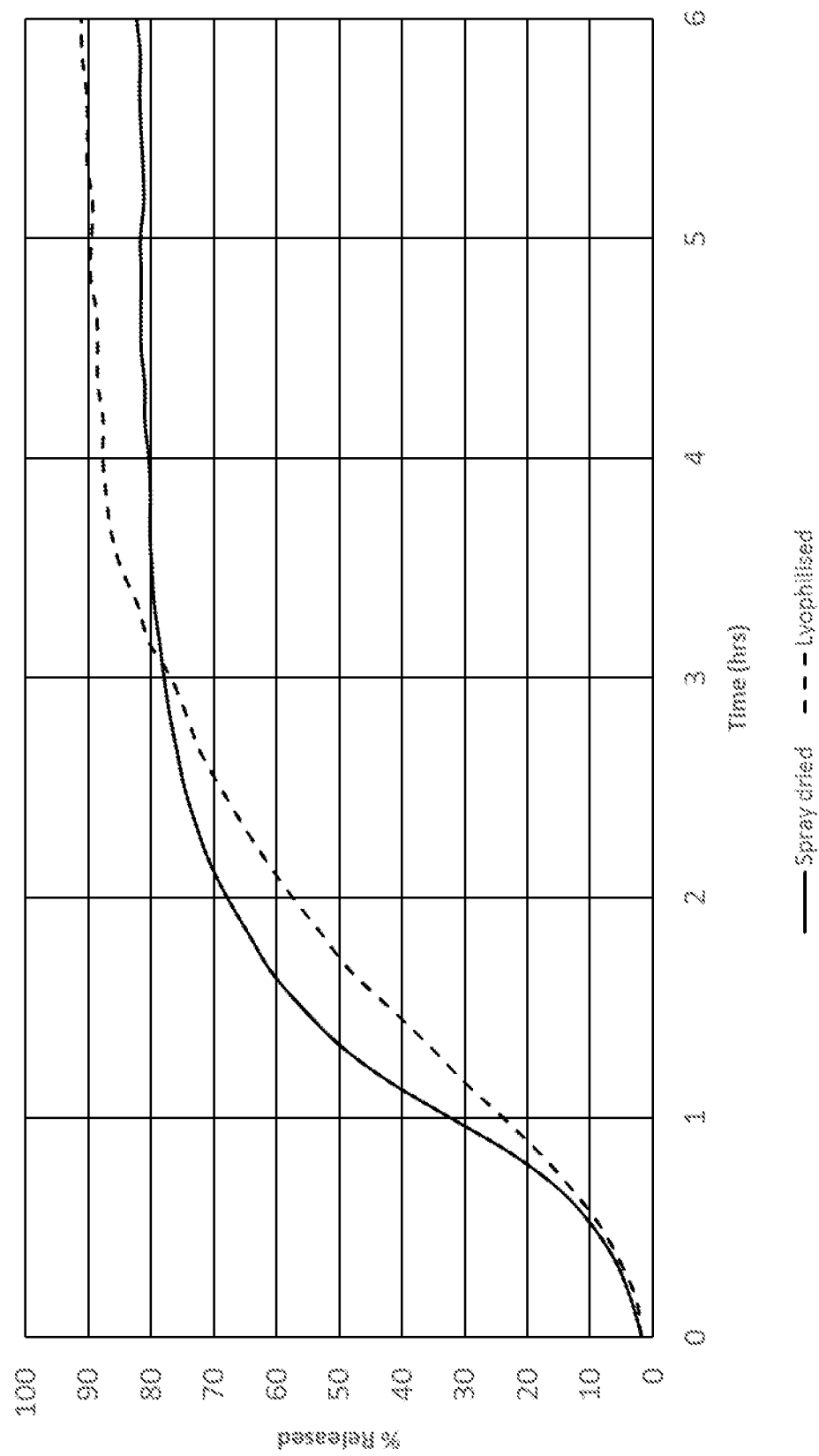

In addition, The Dynamic Dissolution Test was performed. The dissolution profile of the mini-tablets produced using spray-dried material was compared to that of mini-tablets produced previously using lyophilised material (FIG. 12).

The dissolution data on the spray-dried material as expected did not meet the optimal delay period before the coat came off once the pH of the medium had been raised. This was due to the thinner than target coat on these mini-tablets. For this reason, the curves in FIG. 12 for both the lyophilised and spray dried samples have been off-set so that T=0 is the start of release in both instances. Once the coat had come off then the release profile of the ICVD from the mini-tablet cores prepared by spray drying was essentially comparable to ICVD from mini-tablet cores prepared by lyophilisation.

In summary, it was concluded that the spray-dried material processed well in the slugging and compression steps to make mini-tablets and in particular, the resultant dry-granulated material had good flow characteristics. Furthermore, the drug release portion of the dynamic dissolution profile of the mini-tablets produced from spray dried material was essentially comparable to that of the mini-tablets produced from lyophilised material.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps. All patents and patent applications mentioned throughout the specification of the present invention are herein incorporated in their entirety by reference. The invention embraces all combinations of preferred and more preferred groups and suitable and more suitable groups and embodiments of groups recited above.

REFERENCES

Binz et al *Journal of Molecular Biology* 332(2):489-503
Fadda H M et al *Int J Pharm* 2009 382(1-2):56-60
Garbacz et al *European journal of pharmaceutical sciences* 2014 51:224-231
Green and Sambrook *Molecular Cloning: A Laboratory Manual* 2012 $4^{th}$ Edition Cold Spring Harbour Laboratory Press
Goyanes et al *Int J Pharm* 2015 484(1-2):103-108
Griffiths et al *Antibodies* 2013 2:66-81
Hamers-Casterman et al *Nature* 1993 363(6428):446-448
Harmsen et al 2006 *Applied Microbiology and Biotechnology* 72(3):544-551
Hendrickson et al *Clin Microbiol Rev* 2002 15(1):79-94
Hussack et al 2011 *PLOS ONE* 6(11):e28218
Hussan et al 2012 *IOSR Journal of Pharmacy* 2(6):2319-4219
Kabat et al Sequences of Proteins of Immunological Interest, *Fifth Edition U.S. Department of Health and Human Services,* 1991 NIH Publication Number 91-3242
McCoy et al *Retrovirology* 2014 11:83
Merchant et al *Int J Pharm* 2014 475(1-2):585-591
Michael *Immunol Invest* 1989 18(9-10):1049-54
Muyldermans et al *Protein Eng* 1994 7(9):1129-1135
Muyldermans *Annu Rev Biochem* 2013 82:775-797
Padlan *Mol Immunol* 1994 31:169-217
Roux et al *Proc Natl Acad Sci USA* 1998 95:11804-11809
Ungar et al *Clin Gastroenterol Hepatol.* 2016 14(4):550-557
van Schie et al., *Ann Rheum Dis* 2015 74:311-314
Ward et al., *Nature* 1989 341(6242):544-546
Ordas et al. 2012. *Clin Pharmacol Ther.* 91(4). 635-46
Guerra and Bermejo 2014 *Clin Exp Gastroenterol.* 7: 359-367

The invention claimed is:

1. A solid pharmaceutical composition comprising a compressed core, wherein the compressed core comprises:
   (i) a pharmaceutically active binding polypeptide wherein the pharmaceutically active binding polypeptide is present at 40-75% by weight relative to the weight of the core,
   (ii) one or more compression aids wherein the one or more compression aids is present at 20-55% by weight relative to the weight of the core,
   (iii) one or more disintegrants wherein the one or more disintegrants is present at 2-6% by weight relative to the weight of the core and wherein the compressed core is coated with a pH sensitive enteric coating and the pharmaceutically active binding polypeptide is an immunoglobulin or an immunoglobulin fragment.

2. The pharmaceutical composition according to claim 1 wherein the one or more compression aids is selected from the list consisting of synthetic polymers such as crospovidone, saccharides such as sucrose, glucose, lactose and fructose, sugar alcohols such as mannitol, xylitol, maltitol, erythritol, sorbitol, water-soluble polysaccharides such as celluloses such as crystalline cellulose, microcrystalline cellulose, powdered cellulose, hydroxypropylcellulose and methyl cellulose, starches, synthetic polymers such as polyvinylpyrrolidone, sodium starch glycolate, crospovidone and inorganic compounds such as calcium carbonate.

3. The pharmaceutical composition according to claim 1 wherein the one or more disintegrants is selected from the list consisting of carboxymethyl cellulose, sodium carboxymethyl cellulose, croscarmellose sodium, cellulose such as low substitution degree hydroxypropylcellulose, starch such as sodium carboxymethyl starch, hydroxypropyl starch, rice starch, wheat starch, potato starch, maize starch, partly pregelatinized starch.

4. The pharmaceutical composition according to claim 1 comprising one or more lubricants wherein the one or more lubricants is selected from the list consisting of glyceryl behenate, a stearic acid salt such as calcium stearate; magnesium stearate; zinc stearate, mineral oil, polyethylene glycol, sodium lauryl sulfate, sodium stearyl fumarate, starch such as corn starch; potato starch; pregelatinized starch; tapioca starch; wheat starch, stearic acid, talc, vegetable oil and zinc stearate.

5. The pharmaceutical composition according to claim 1 comprising one or more lubricants wherein the one or more lubricants is present at 0.1-2%, such as about 1% by weight relative to the weight of the core.

6. The pharmaceutical composition according to claim 1 wherein the pharmaceutically active binding polypeptide is present at about 50%-60% by weight relative to the weight of the core.

7. The pharmaceutical composition according to claim 1 wherein the pH sensitive enteric coating has a thickness of 10-300 um.

8. The pharmaceutical composition according to claim 1 wherein the pH sensitive enteric coating comprises or consists of a pH sensitive enteric polymer coat optionally together with one or more of a plasticiser, an anti-tacking agent and a surfactant.

9. The pharmaceutical composition according to claim 8 wherein the pH sensitive enteric polymer coat comprises one or more of: methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid.

10. The pharmaceutical composition according to claim 8 wherein the pH sensitive enteric polymer coat does not dissolve until after 2 hours or longer exposure to a pH between 0.5 and 3.5.

11. The pharmaceutical composition according to claim 1 wherein the molecular weight of the pharmaceutically active binding polypeptide is 5-200 kD.

12. The pharmaceutical composition according to claim 1 wherein the pharmaceutically active binding polypeptide has an aqueous solubility of greater than 10 mg/mL, such as greater than 30 mg/mL.

13. The pharmaceutical composition according to claim 1 wherein the immunoglobulin fragment is an immunoglobulin chain variable domain (ICVD).

14. The pharmaceutical composition according to claim 13 wherein the immunoglobulin chain variable domain is an immunoglobulin heavy chain variable domain.

15. The pharmaceutical composition according to claim 13 wherein the immunoglobulin chain variable domain is an immunoglobulin heavy chain variable domain from a conventional antibody (a VH) or an immunoglobulin heavy chain variable domain from a heavy chain antibody (a VHH).

16. The pharmaceutical composition according to claim 1 wherein when assayed in the Pharmacopeia! Dissolution Test, the pharmaceutical composition releases:
  (i). 10-40% by weight of the pharmaceutically active binding polypeptide after 30 minutes,
  (ii). 30-60% by weight of the pharmaceutically active binding polypeptide after 60 minutes and
  (iii). 60% by weight or greater of the pharmaceutically active binding polypeptide after 120 minutes.

17. The pharmaceutical composition according to claim 1 wherein when assayed in the Dynamic Dissolution Test:
  the start of release of the pharmaceutical composition occurs between 90 to 210 minutes, the pharmaceutical composition releases:
  (i). 10-30% by weight of the pharmaceutically active binding polypeptide after 60 minutes from start of release,
  (ii). 40-70% by weight of the pharmaceutically active binding polypeptide after 120 minutes from start of release and
  (iii). 60% by weight or greater of the pharmaceutically active binding polypeptide after 180 minutes from start of release.

18. The pharmaceutical composition according to claim 1 wherein when assayed in the Pharmacopeial Enteric Coating Test, the pharmaceutical composition releases less than 10% by weight of the pharmaceutically active binding polypeptide after 2 hours.

19. The pharmaceutical composition according to claim 1 wherein the pharmaceutically active binding polypeptide comprises or consists of any one of SEQ ID NOs: 1 to 28.

20. A method of delivering a pharmaceutically active binding polypeptide of claim 1 to a region of the intestinal tract comprising orally administering said solid pharmaceutical composition comprising said compressed core, wherein the compressed core comprises said pharmaceutically active binding polypeptide and wherein the compressed core is coated with a pH sensitive enteric coating.

21. The method according to claim 20 wherein the pH sensitive enteric coating releases pharmaceutically active binding polypeptide when exposed to a region of the intestinal tract.

* * * * *

UNITED STATES PATENT AND TRADEMARK OFFICE
CERTIFICATE OF CORRECTION

Page 1 of 1

PATENT NO. : 10,772,839 B2
APPLICATION NO. : 16/140843
DATED : September 15, 2020
INVENTOR(S) : Scott Crowe et al.

It is certified that error appears in the above-identified patent and that said Letters Patent is hereby corrected as shown below:

In the Claims

At Column 62, Claim number 16, Line number 11, please replace "Pharmacopeia!" with
-- Pharmacopeial --

Signed and Sealed this
Fifth Day of January, 2021

Andrei Iancu
*Director of the United States Patent and Trademark Office*